(12) United States Patent
Micanovic et al.

(10) Patent No.: US 6,835,814 B1
(45) Date of Patent: Dec. 28, 2004

(54) PROTEASE RESISTANT FLINT ANALOGS

(75) Inventors: Radmila Micanovic, Indianapolis, IN (US); Radhakrishnan Rathnachalam, Carmel, IN (US); Derrick Ryan Witcher, Fishers, IN (US)

(73) Assignee: Eli Lilly and Company, Indianapolis (IN)

( * ) Notice: Subject to any disclaimer, the term of this patent is extended or adjusted under 35 U.S.C. 154(b) by 0 days.

(21) Appl. No.: 09/936,019

(22) PCT Filed: Mar. 20, 2000

(86) PCT No.: PCT/US00/06418
§ 371 (c)(1),
(2), (4) Date: Sep. 7, 2001

(87) PCT Pub. No.: WO00/58466
PCT Pub. Date: Oct. 5, 2000

Related U.S. Application Data

(60) Provisional application No. 60/126,839, filed on Mar. 30, 1999, provisional application No. 60/140,073, filed on Jun. 21, 1999, provisional application No. 60/147,071, filed on Aug. 4, 1999, provisional application No. 60/160,524, filed on Oct. 20, 1999, provisional application No. 60/160,669, filed on Oct. 21, 1999, provisional application No. 60/172,744, filed on Dec. 20, 1999, and provisional application No. 60/178,184, filed on Jan. 26, 2000.

(51) Int. Cl.[7] .................. C07K 14/705; C07H 21/04
(52) U.S. Cl. .................. 530/350; 536/23.5; 514/12
(58) Field of Search .................. 530/350; 424/45, 424/46

(56) References Cited

U.S. PATENT DOCUMENTS 5,688,664 A * 11/1997 Dawson et al. ............ 435/69.2

FOREIGN PATENT DOCUMENTS

| WO | WO 98 30694 | 7/1998 |
| WO | WO99 04001 | 1/1999 |
| WO | WO 99 14330 | 3/1999 |

OTHER PUBLICATIONS

Suidan et al.,, Proc. Natl. Acad. Sci. SUA, vol. 91, pp. 8112–8116, Aug. 1994.*

* cited by examiner

Primary Examiner—Lorraine Spector
Assistant Examiner—Eileen B O'Hara
(74) Attorney, Agent, or Firm—Thomas D. Webster

(57) ABSTRACT

The invention relates to FLINT analogs that are to proteolysis in vivo and in vitro at amino acid position 218 of mature FLINT, clinical and therapeutic uses thereof, and pharmaceutical formulations comprising said analogs.

**6

PROTEASE RESISTANT FLINT ANALOGS

CROSS-REFERENCE

Figure 1:
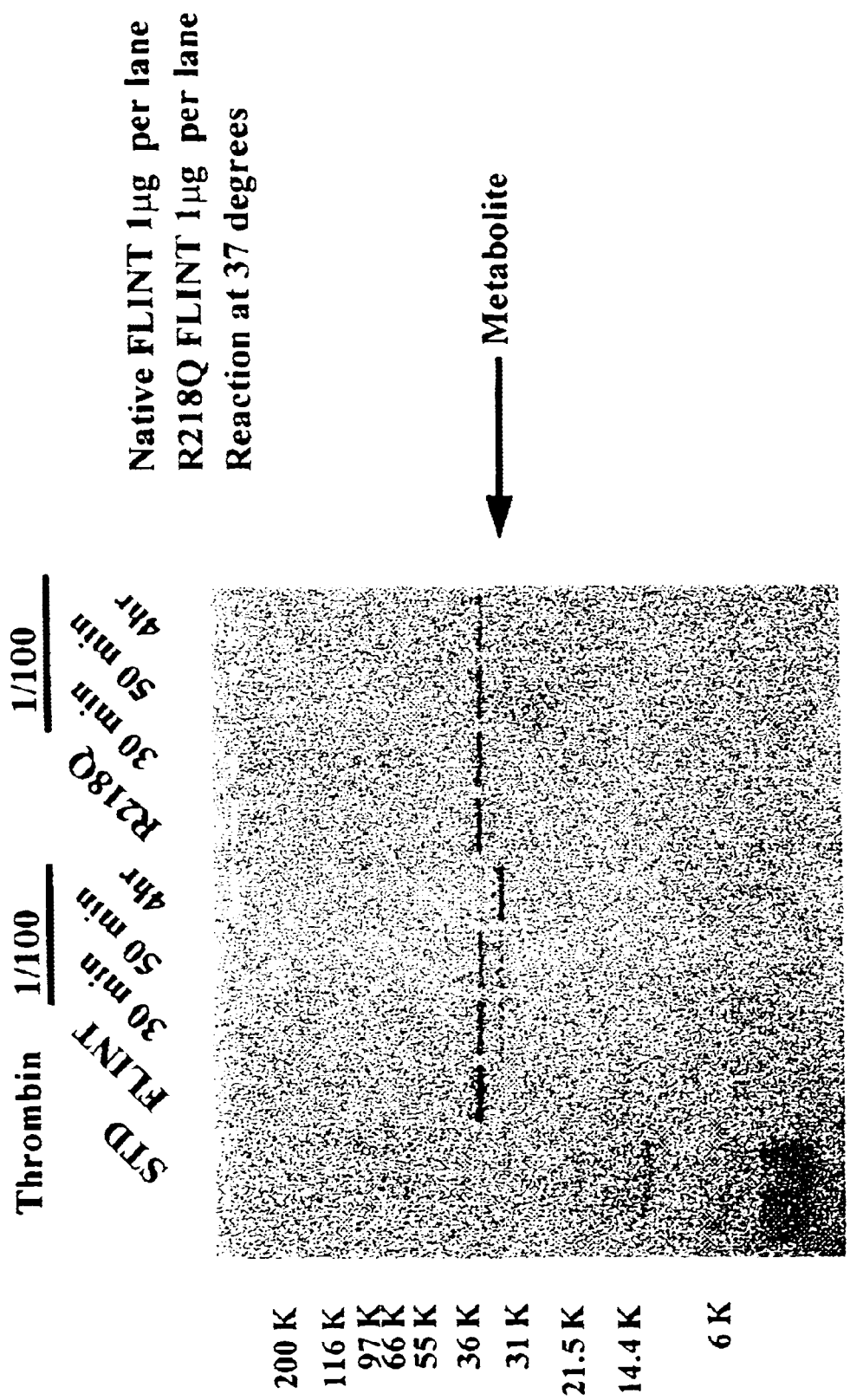

This application claims the benefit of U.S. Provisional Application Nos. 60/126,839, filed Mar. 30, 1999; 60/140,073, filed Jun. 21, 1999; 60/147,071, filed Aug. 4, 1999; 60/160,524, filed Oct. 20, 1999; 60/160,669, filed Oct. 21, 1999; 60/172,744, filed Dec. 20, 1999; and No. 60/178,184, filed Jan. 26, 2000.

BACKGROUND OF THE INVENTION

A number of tumor necrosis factor receptor proteins ("TNFR proteins") have been isolated in recent years, having many potent biological effects. Aberrant activity of these proteins has been implicated in a number of disease states.

One such TNFR homologue, referred to herein as "FASLigand Inhibitory Protein" or "FLINT", binds FAS Ligand (FAS L) thereby preventing the interaction of FAS L with FAS (See U.S. Provisional Applications Ser. Nos. 60/112,577, 60/112,933, and 60/113,407, filed Dec. 17, 18 and 22, 1998, respectively, the entire teachings of which are incorporated herein by reference).

Increased activation of the FAS-FAS Ligand signal transduction pathway is implicated in a number of pathological conditions, including runaway apoptosis (Kondo et al., Nature Medicine 3(4):409–413 (1997); Galle et al., *J. Exp. Med.* 182:1223–1230 (1995)), and inflammatory disease resulting from neutrophil activation (Miwa et al.,. *Nature Medicine* 4:1287 (1998)).

"Runaway apoptosis" is a level of apoptosis greater than normal, or apoptosis occurring at an inappropriate time. Pathological conditions caused by runaway apoptosis include, for example, organ failure in the liver, kidneys and pancreas. Inflammatory diseases associated with excessive neutrophil activation include sepsis, ARDS, SIRS and MODS.

Compounds such as FLINT, which inhibit the binding of FAS to FASL, and LIGHT to LTβR and/or TR2/HVEM receptors, can be used to treat or prevent diseases or conditions that may be associated with these binding interactions. The therapeutic utility of FLINT could be enhanced by FLINT analogs that exhibit modified pharmacological properties (e.g., enhanced potency, and/or longer in vivo half-lives, and/or greater affinity for FASL), modified pharmaceutical properties (e.g., decreased aggregation and surface adsorption, increased solubility and ease of formulation) and/or modified physical properties such as susceptibility to proteolysis.

SUMMARY OF THE INVENTION

The FLINT polypeptide undergoes proteolysis in vivo to produce at least two major peptide fragments. One of the fragments consists of residues 1 through 218 of SEQ ID NO:1 (alternatively residues 1 through 247 of SEQ ID NO.:3), termed herein "FLINT metabolite;" the other consists of residues 219 through 271 of SEQ ID NO:1 (alternatively residues 248 through 300 of SEQ ID NO:3). Cleavage at the 218 position in vitro can be achieved when native FLINT (SEQ ID NO:3), or mature FLINT (SEQ ID NO:1), is treated with a trypsin-like enzyme, for example, thrombin, trypsin or other serine protease. Thus it is likely that a serine protease is responsible for the in vivo proteolysis of FLINT. Production of FLINT metabolite is disclosed in co-pending U.S. patent application Ser. No. 09/936,024, herein incorporated by reference.

In vitro studies suggest that FLINT metabolite binds FasL with an apparent lower affinity than FLINT. Therefore, the pharmaceutical utility of FLINT could be enhanced by an analog that is resistant to proteolysis at or near the 218 position. The invention disclosed herein provides such analogs.

In one embodiment, the invention relates to a FLINT analog that is resistant to proteolysis between positions 218 and 219 of SEQ ID NO:1, and/or between positions 247 and 248 of SEQ ID NO:3 in vivo and/or in vitro.

In another embodiment, the invention relates to a FLINT analog that is substantially resistant to proteolysis between positions 218 and 219 of SEQ ID NO:1, and/or between positions 247 and 248 of SEQ ID NO:3 in vivo and/or in vitro.

In another embodiment, the invention relates to a FLINT C) analog that is resistant to proteolysis by a trypsin-like protease between positions 218 and 219 of SEQ ID NO:1, and/or between positions 247 and 248 of SEQ ID NO: 3 in vivo and/or in vitro.

In another embodiment, the invention relates to a FLINT analog that is resistant to proteolysis by a serine protease, for example, trypsin, thrombin, or chymotrypsin between positions 218 and 219 of SEQ ID NO:1, and/or between positions 247 and 248 of SEQ ID NO:3, in vivo and/or in vitro.

In another embodiment, the invention relates to a FLINT analog that is resistant to proteolysis by a trypsin-like protease between positions 218 and 219 of SEQ ID NO:1, and/or between positions 247 and 248 of SEQ ID NO:3, said analog comprising a polypeptide that is at least about 80% identical; alternatively at least about 90% identical; alternatively at least about 95% identical; alternatively at least 96% identical; alternatively at least 97% identical; alternatively at least 98% identical; alternatively still, at least 99% identical with SEQ ID NO:1 and/or SEQ ID NO:3.

In another embodiment, the invention relates to a FLINT analog that is resistant to proteolysis by a trypsin-like protease between positions 218 and 219 of SEQ ID NO:1, and/or between positions 247 and 248 of SEQ ID NO:3, said analog comprising a polypeptide that is at least about 10% identical; alternatively at least 20% identical; alternatively at least 30% identical; alternatively at least 40% identical; alternatively at least 50% identical; alternatively at least 60% identical; alternatively at least 70% identical, alternatively at least 80% identical, alternatively still, at least 90% identical with residues 214 through 222 of SEQ ID NO:1 and/or residues 243 through 251 of SEQ ID NO:3.

In another embodiment, the invention relates to a FLINT analog comprising one or more amino acid substitutions) deletion(s), or addition(s) in the region comprising amino acids 214–222 of SEQ ID NO:1 and/or amino acids 243–251 of SEQ ID NO:3.

In another embodiment, the invention relates to a FLINT analog comprising one or more amino acid substitutions), deletions, or addition(s) in the region comprising amino acids 215–218 of SEQ ID NO:1 and/or amino acids 243–251 of SEQ ID NO:3.

In another embodiment, the invention relates to a FLINT analog comprising one or more amino acid substitution(s) in the region 214–222 of SEQ ID NO:1, and/or amino acids 243–251 of SEQ ID NO:3.

In another embodiment, the invention relates to a FLINT analog comprising an amino acid substitution (s) in the region comprising amino acids 214–222 of SEQ ID NO:1, selected from the group consisting of:

a. Pro at position 215 is replaced by any naturally occurring amino acid other than Pro;

b. Thr at position 216 is replaced by any naturally occurring amino acid other than Thr;

c. Pro at position 217 is replaced by any naturally occurring amino acid other than Pro;

d. Arg at position 218 is replaced by any naturally occurring amino acid other than Arg;

e. Ala at position 219 is replaced by any naturally occurring amino acid other than Ala;

f. Gly at position 220 is replaced by any naturally occurring amino acid other than Gly;

g. Arg at position 221 is replaced by any naturally occurring amino acid other than Arg;

h. Ala at position 222 is replaced by any naturally occurring amino acid other than Ala.

In another embodiment, the invention relates to a FLINT analog comprising an amino acid substitution in the region comprising amino acids 214–222 of SEQ ID NO:1, selected from the group consisting of:

a. Gly at position 214 is replaced by a positively charged amino acid that is not Gly;

b. Pro at position 215 is replaced by a positively charged amino acid that is not Pro;

c. Thr at position 216 is replaced by a positively charged amino acid that is not Thr;

d. Pro at position 217 is replaced by a positively charged amino acid that is not Pro;

e. Arg at position 218 is replaced by a positively charged amino acid that is not Arg;

f. Ala at position 219 is replaced by a positively charged amino acid that is not Ala;

g. Gly at position 220 is replaced by a positively charged amino acid that is not Gly;

h. Arg at position 221 is replaced by a positively charged amino acid that is not Arg;

i. Ala at position 222 is replaced by a positively charged amino acid that is not Ala.

In another embodiment, the invention relates to a FLINT analog comprising an amino acid substitution in the region comprising amino acids 214–222 of SEQ ID NO:1, selected from the group consisting of:

a. Gly at position 214 is replaced by a negatively charged amino acid that is not Gly;

b. Pro at position 215 is replaced by a negatively charged amino acid that is not Pro;

c. Thr at position 216 is replaced by a negatively charged amino acid that is not Thr;

d. Pro at position 217 is replaced by a negatively charged amino acid that is not Pro;

e. Arg at position 218 is replaced by a negatively charged amino acid that is not Arg;

f. Ala at position 219 is replaced by a negatively charged amino acid that is not Ala;

g. Gly at position 220 is replaced by a negatively charged amino acid that is not Gly;

h. Arg at position 221 is replaced by a negatively charged amino acid that is not Arg;

i. Ala at position 222 is replaced by a negatively charged amino acid that is not Ala.

In another embodiment, the invention relates to a FLINT analog comprising an amino acid substitution in the region comprising amino acids 214–222 of SEQ ID NO:1, selected from the group consisting of:

a. Gly at position 214 is replaced by a polar uncharged amino acid that is not Gly;

b. Pro at position 215 is replaced by a polar uncharged amino acid that is not Pro;

c. Thr at position 216 is replaced by a polar uncharged amino acid that is not Thr;

d. Pro at position 217 is replaced by a polar uncharged amino acid that is not Pro;

e. Arg at position 218 is replaced by a polar uncharged amino acid that is not Arg;

f. Ala at position 219 is replaced by a polar uncharged amino acid that is not Ala;

g. Gly at position 220 is replaced by a polar uncharged amino acid that is not Gly;

h. Arg at position 221 is replaced by a polar uncharged amino acid that is not Arg;

i. Ala at position 222 is replaced by a polar uncharged amino acid that is not Ala.

In another embodiment, the invention relates to a FLINT analog comprising an amino acid substitution in the region comprising amino acids 214–222 of SEQ ID NO:1, selected from the group consisting of:

a. Gly at position 214 is replaced by a nonpolar amino acid that is not Gly;

b. Pro at position 215 is replaced by a nonpolar amino acid that is not Pro;

c. Thr at position 216 is replaced by a nonpolar amino acid that is not Thr;

d. Pro at position 217 is replaced by a nonpolar amino acid that is not Pro;

e. Arg at position 218 is replaced by a nonpolar amino acid that is not Arg;

f. Ala at position 219 is replaced by a nonpolar amino acid that is not Ala;

g. Gly at position 220 is replaced by a nonpolar amino acid that is not Gly;

h. Arg at position 221 is replaced by a nonpolar amino acid that is not Arg;

i. Ala at position 222 is replaced by a nonpolar amino acid that is not Ala.

In another embodiment, the invention relates to a FLINT analog comprising an amino acid substitution in the region comprising amino acids 214–222 of SEQ ID NO:1, selected from the group consisting of:

a. Arg at position 218 is replaced by Gln;

b. Arg at position 218 is replaced by Glu;

c. Thr at position 216 is replaced by Pro;

d. Arg at position 218 is replaced by Ala;

e. Arg at position 218 is replaced by Gly;

f. Arg at position 218 is replaced by Ser;

g. Arg at position 218 is replaced by Val h. Arg at position 218 is replaced by Tyr;

i. Pro at position 217 is replaced by Tyr j. Thr at position 216 is replaced by Pro, and Arg at position 218 is replaced by Gln.

In another embodiment, the present invention relates to a FLINT analog comprising SEQ ID NO:1 wherein Arg at position 34 is replaced by Asn, Asp at position 36 is replaced by Thr, and Arg at position 218 is replaced by Gln, Glu, Ala, Gly, Ser. Val, or Tyr.

In another embodiment, the present invention relates to a FLINT analog comprising SEQ ID NO:1 wherein Arg at position 34 is replaced by Asn, Asp at position 36 is replaced by Thr, Asp at position 194 is replaced by Asn, Ser at position 196 is replaced by Thr, and Arg at position 218 is replaced by Gln, Glu, Ala, Gly, Ser, Val, or Tyr.

In another embodiment, the present invention relates to a FLINT analog comprising one or more amino acid substitution(s) within SEQ ID NO:1 wherein Arg at position 34 is replaced by Asn, Asp at position 36 is replaced by Thr, and Arg at position 218 is replaced by an amino acid selected from the group consisting of:

a. any naturally occurring amino acid that is not Arg;
  b. any positively charged amino acid that is not Arg;
  c. any negatively charged amino acid that is not Arg;
  d. any polar uncharged amino acid that is not Arg;
  e. any nonpolar amino acid that is not Arg; and
  f. an amino acid that is Glu, Gln, Ala, Gly, Ser, Val, or Tyr.

In another embodiment, the present invention relates to a FLINT analog comprising one or more amino acid substitutions within SEQ ID NO:1 wherein Arg at position 34 is replaced by Asn, Asp at position 36 is replaced by Thr, Asp at position 194 is replaced by Asn, Ser at position 196 is replaced by Thr, and Arg at position 218 is replaced by an amino acid selected from the group consisting of:

a. any naturally occurring amino acid that is not Arg;
  b. any positively charged amino acid that is not Arg;
  c. any negatively charged amino acid that is not Arg;
  d. any polar uncharged amino acid that is not Arg;
  e. any nonpolar amino acid that is not Arg; and
  f. an amino acid that is Glu, Gln, Ala, Gly, Ser, Val, or Tyr.

In another embodiment, the present invention relates to a FLINT analog comprising one or more amino acid substitution(s) within SEQ ID NO:1 wherein Ser at position 132 is replaced by Asn, and Arg at position 218 is replaced by an amino acid selected from the group consisting of:

a. any naturally occurring amino acid that is not Arg;
  b. any positively charged amino acid that is not Arg;
  c. any negatively charged amino acid that is not Arg;
  d. any polar uncharged amino acid that is not Arg;
  e. any nonpolar amino acid that is not Arg; and
  f. an amino acid that is Glu, Gln, Ala, Gly, Ser, Val, or Tyr.

Another embodiment relates to a nucleic acid encoding a protease-resistant FLINT analog of the present invention.

In another embodiment, the invention relates to a protease resistant FLINT analog that is encoded by a nucleic acid that hybridizes to SEQ ID NO:2 under high stringency conditions.

In another embodiment, the present invention relates to a nucleic acid that encodes a protease resistant FLINT analog, said nucleic acid hybridizing to SEQ ID NO:2 under high stringency conditions.

In another embodiment, the present invention relates to a vector comprising a nucleic acid encoding a protease-resistant FLINT analog.

In another embodiment the invention relates to therapeutic and clinical uses of a protease resistant FLINT analog to prevent or treat a disease or condition in a mammal in need of such prevention or treatment.

In another embodiment the invention relates to therapeutic and clinical uses of a protease resistant FLINT analog to prevent or treat acute lung injury (ALI), acute respiratory distress syndrome (ARDS), ulcerative colitis, and to facilitate organ preservation for transplantation.

In another embodiment the present invention relates to a pharmaceutical composition comprising a protease resistant FLINT analog.

In another embodiment the present invention relates to the use of FLINT analog to inhibit T lymphocyte activation.

In another embodiment, the present invention relates to the use of FLINT analog to prevent or treat chronic obstructive pulmonary disease (COPD).

In another embodiment, the present invention relates to the use of FLINT analog to prevent or treat pulmonary fibrosis (PF).

In another embodiment, the present invention relates to a method for producing a protease resistant FLINT analog, said analog being resistant to proteolysis by a trypsin-like protease between positions 218 and 219 of SEQ ID NO:1 (alternatively between positions 247 and 248 of SEQ ID NO:3), comprising the step of altering the amino acid sequence in the region at and/or between positions 214 to 222 of SEQ ID NO:1, as described herein.

DETAILED DESCRIPTION OF THE INVENTION

SEQ ID NO:1—Mature human FLINT, i.e. native FLINT minus the leader sequence.

SEQ ID NO:2—Nucleic acid/cDNA encoding mature human FLINT.

SEQ ID NO:3—Native human FLINT.

SEQ ID NO:4—Human FLINT leader sequence.

SEQ ID NO:5—Oligonucleotide primer A, CF107

SEQ ID NO:6—Oligonucleotide primer B, CF111

SEQ ID NO:7—Oligonucleotide primer C, CF112

SEQ ID NO:8—Oligonucleotide primer D, CF110

SEQ ID NO:9—Nucleic acid/cDNA encoding native human FLINT.

FIG. 1. Time course thrombin cleavage of native FLINT and R218Q analog.

Figure 2:
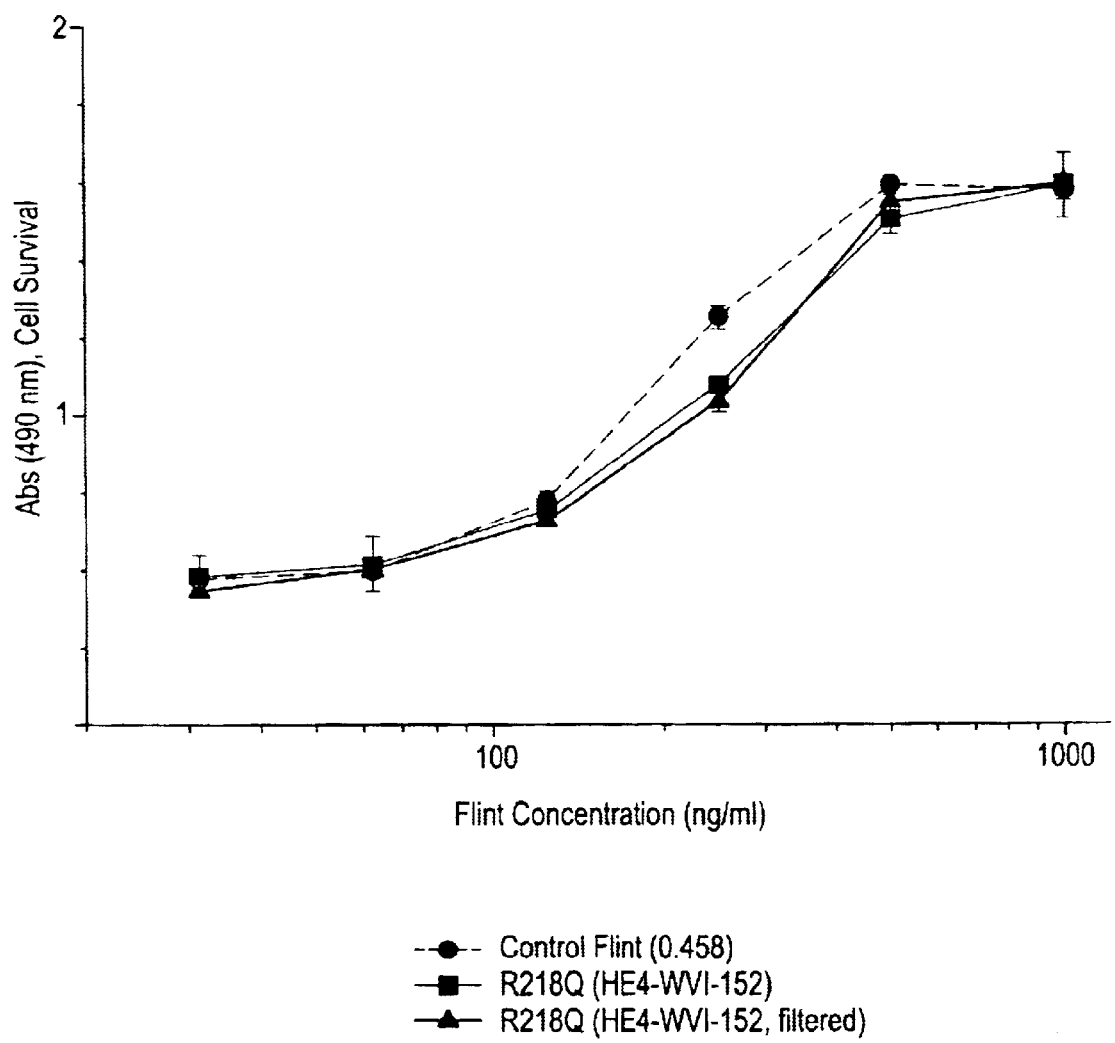

FIG. 2. FLINT analog R218Q inhibits FasL-induced apoptosis in Jurkat cells. FLINT samples purified from AV12 cells.

Figure 3:
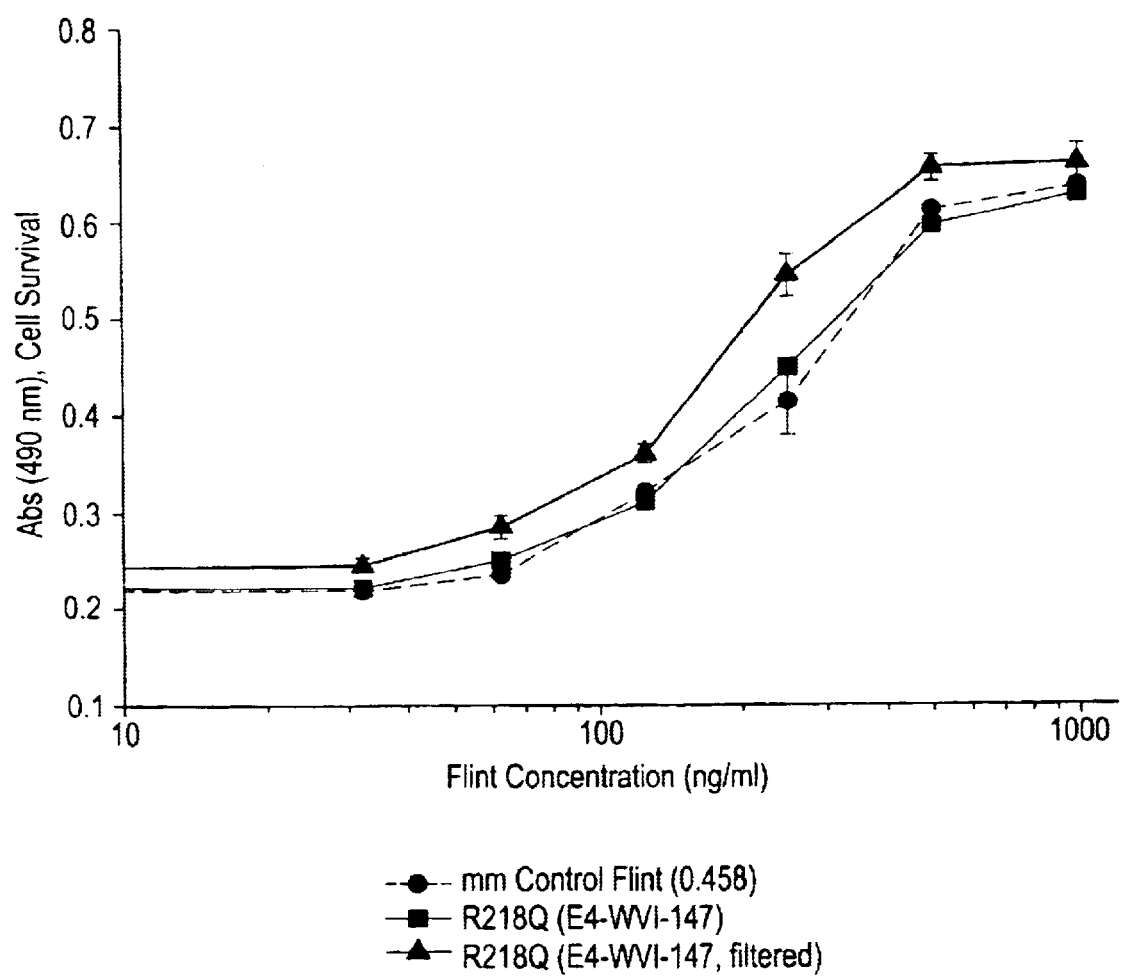

FIG. 3. FLINT analog R218Q purified from 293 EBNA cells inhibits FasL induced apoptosis in Jurkat cells.

Figure 4:
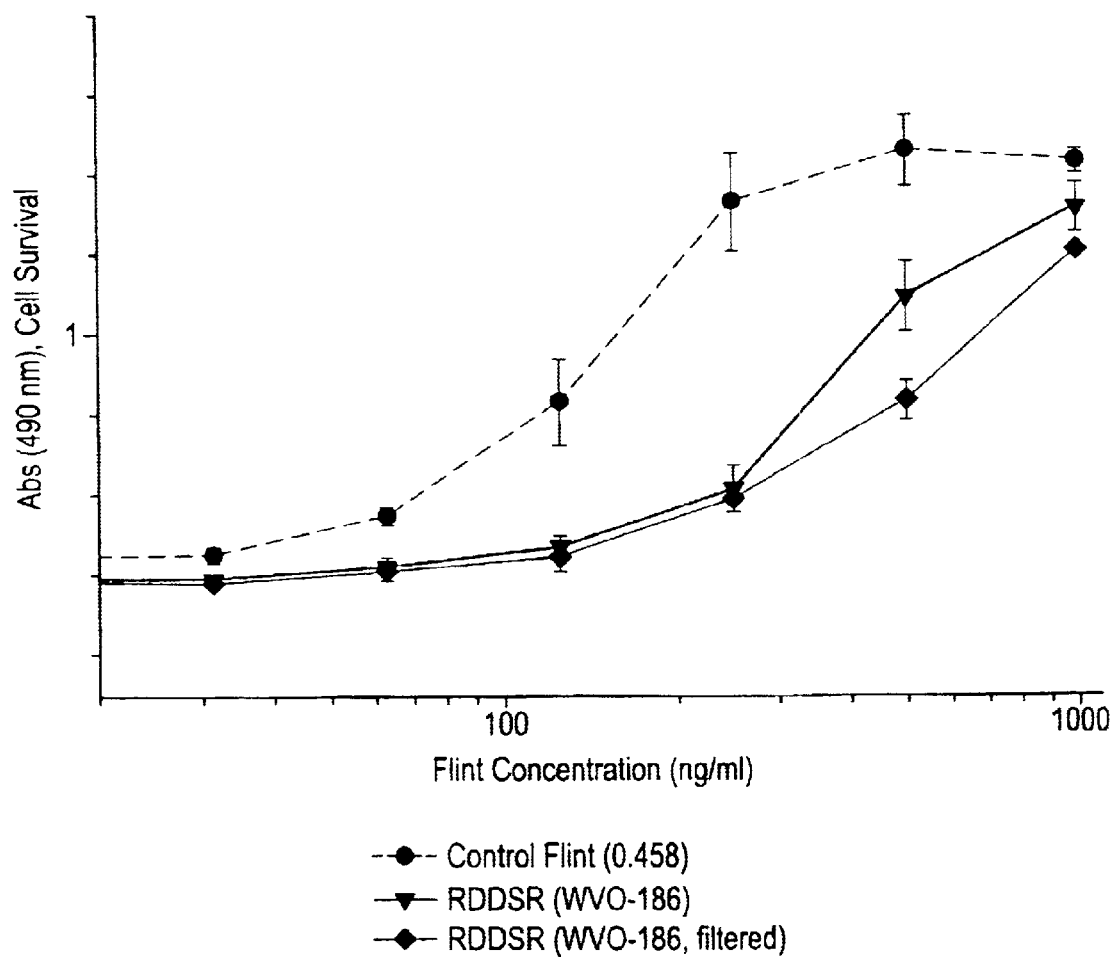

FIG. 4. FLINT analog RDDSR inhibits FasL-induced apoptosis in Jurkat cells.

Figure 5A:
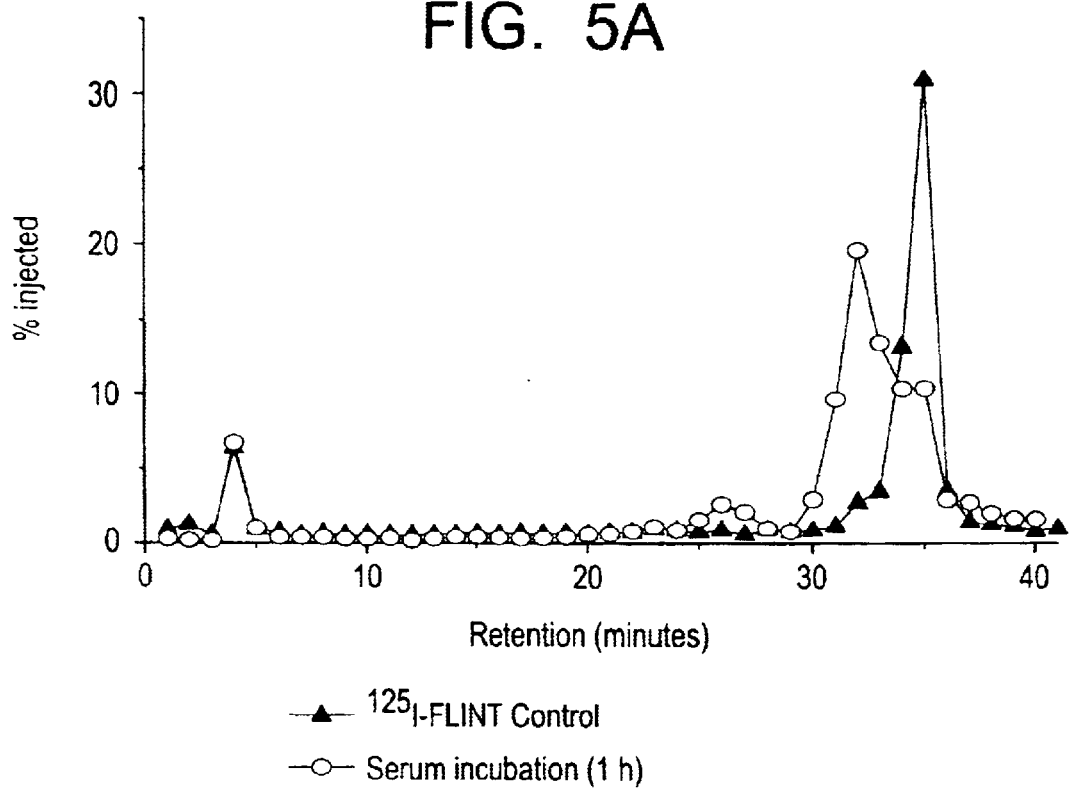

FIG. 5. RP-HPLC profile of radioactivity after an in vitro incubation of $^{125}$I-FLINT and $^{125}$I-FLINT(R218Q) with ICR mouse blood. Test articles were incubated for 1 h at 37° C. Serum was prepared and fractionated by RP-HPLC. Data is expressed as the percentage of radioactivity per fraction applied to the column.

FIG. 6. RP-HPLC profile of FLINT immunoreactivity in plasma 15 min. after an intravenous administration of FLINT, or FLINT (R218Q), to ICR mice. Fractions were collected and analyzed by ELISA. Data are representative of findings from each individual animal.

Figure 7:
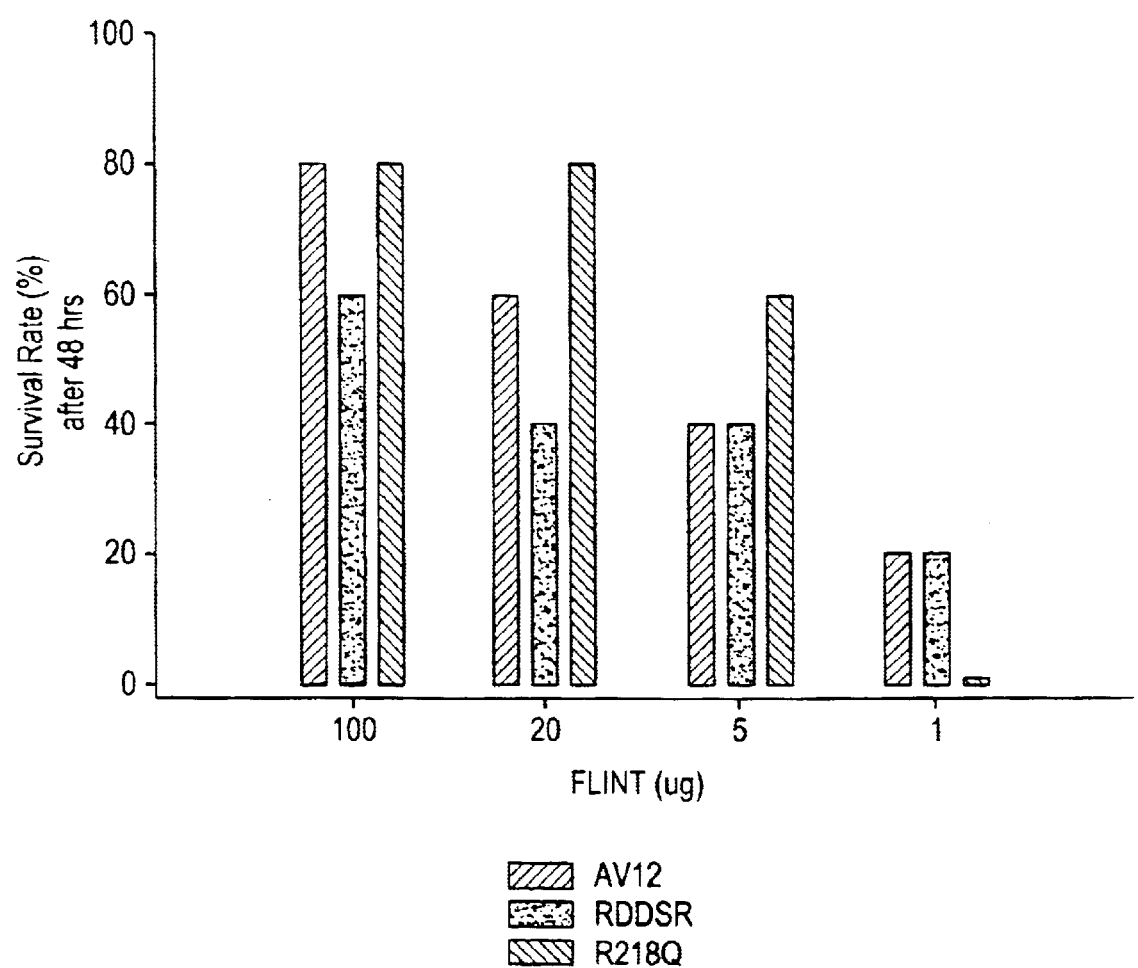

FIG. 7. FLINT and FLINT analog dose response in mouse acute liver failure (ALF) model.

The term "analog" or "FLINT analog" means a variant FLINT, or fragment thereof, resistant to proteolysis between positions 218 and 219 of SEQ ID NO:1 (positions 247 and 248 of SEQ ID NO:3), and which preferably has biological activity substantially the same as FLINT.

The term "negatively charged group" or "negatively charged amino acid" refers to Asp or Glu.

The term "positively charge group" or "positively charged amino acid" refers to His, Arg, or Lys.

The term "polar uncharged" or "polar uncharged amino acid" refers to Cys, Thr, Ser, Gly, Asn, Gln, and Tyr.

The term "nonpolar" or "nonpolar amino acid" refers to Ala, Pro, Met, Leu, Ile, Val, Phe, or Trp.

The term "naturally-occurring amino acid" refers to any of the 20 L-amino acids that are found in proteins.

The term "native FLINT" refers to SEQ ID NO:3.

The term "mature FLINT" refers to SEQ ID NO:1.

The term "FLINT" refers to native and mature FLINT from human, other primates, and other mammalian and non-mammalian sources.

As used herein "half-life" refers to the time required for approximately half of FLINT or FLINT analog molecules in a sample to be proteolytically cleaved between positions 218 and 219 of SEQ ID NO:1, in vitro and/or in vivo, as determined by any suitable means.

The term oprotease-resistantm or "resistant" refers to a FLINT analog that, when compared with FLINT, or FLINT fragment, is more resistant to proteolysis between residues 218 and 219 of SEQ ID NO:1. Protease resistant analogs differ from FLINT by one or more amino acid substitutions, deletions, inversions, additions, and/or changes in glycosylation sites, or patterns, as compared with or against native FLINT, or mature FLINT, or other FLINT fragment. Preferably these changes occur in the region from about position 214 through position 222 of SEQ ID NO:1.

The term "protease-resistant" contemplates degrees of resistance to proteolysis at position 218 from complete resistance to partial resistance. Thus, a "substantially resistant" analog shows a degree of resistance to proteolysis at position 218, for example, an analog with a half-life that is at least about 25% greater than native FLINT when treated or exposed to a suitable protease. Preferably, a substantially resistant FLINT analog possesses a protease resistance half-life that is at least about 2-fold greater than native FLINT.

Susceptibility to proteolysis will depend on factors such as the amino acid sequence at or near the site of cleavage and/or the recognition site for the particular proteolytic enzyme involved, and on the physical and chemical environment of the particular analog under consideration. Such factors can affect the $K_M$ and/or rate of proteolysis by a proteolytic enzyme.

The recognition site for serine proteases including thrombin has been investigated. Thrombin will cleave at multiple sites including LVPR/ and sites related to LVPR/, e.g. VDPR/ as well as others. Charge density and steric properties operative at an enzyme's active site will determine the degree to which proteolysis occurs. Thus, the present invention contemplates protease resistant analogs of FLINT that comprise one or more amino acid substitutions, deletions, or additions within a window defined by residues 215 through 218 of SEQ ID NO:1. Such analogs are easily constructed by the skilled artisan using known recombinant techniques and testable in vitro for resistance to proteolysis at position 218. All such embodiments are intended to be within the scope of the present invention.

Protease resistance, as contemplated herein, refers to the sensitivity of a FLINT analog to proteolysis at position 218, in vivo or in vitro. For example, the resistance of an analog to a trypsin-like protease such as thrombin or trypsin, or other serine protease is compared with the resistance shown by FLINT under the same conditions. It is preferred that a FLINT analog display a half-life at least 5% greater than FLINT, alternatively at least 10%, 20%, 30%, 40%, or between 50% to 100% greater than wild type FLINT, as determined by the relative quantity of full length molecules to smaller digestion products (e.g. fragments 1–218 and 219–271 of SEQ ID NO:1). Any suitable method for making a qualitative and/or quantitative assessment of said relative quantities can be used, for example, polyacrylamide gel electrophoresis. Most preferably, a resistant analog possesses a half-life that is from about 1-fold to 2-fold greater than FLINT to about 100-fold or greater than FLINT.

"Fragment thereof" refers to a fragment, piece, or subregion of a FLINT nucleic acid or protein molecule or analog of the present invention, such that the fragment comprises 5 or more amino acids, or 10 or more nucleotides that are contiguous in the parent protein or nucleic acid molecule.

The term "fusion protein" denotes a hybrid protein molecule not found in nature comprising a translational fusion or enzymatic fusion in which two or more different proteins or fragments thereof are covalently linked on a single polypeptide chain.

"Functional fragment" or functionally equivalent fragment, as used herein, refers to a region, or fragment of a full length protein of the present invention that are capable of providing a substantially similar biological activity as a full length protein of the invention, in vivo and/or in vitro, viz. the capacity to inhibit apoptosis. Functional fragments may be produced by cloning technology, or as the natural products of alternative splicing mechanisms.

"Host cell" refers to any eucaryotic or procaryotic cell that is suitable for propagating and/or expressing a cloned gene or nucleic acid contained on a vector that is introduced into said host cell by, for example, transformation or transfection, or the like.

The term "hybridization" as used herein refers to a process in which a single-stranded nucleic acid molecule joins with a complementary strand through nucleotide base pairing. "Selective hybridization" refers to hybridization under conditions of high stringency. The degree of hybridization depends upon the degree of homology, the stringency of hybridization, and the length of hybridizing strands.

"Isolated nucleic acid compound" refers to any RNA or DNA sequence, however constructed or synthesized, which is locationally distinct from its natural location.

The term "stringency" refers to hybridization conditions. High stringency conditions disfavor non-homologous base pairing. Low stringency conditions have the opposite effect. Stringency may be altered, for example, by temperature and salt concentration.

"Low stringency" conditions comprise, for example, a temperature of about 37° C. or less, a formamide concentration of less than about 50%, and a moderate to low salt (SSC) concentration; or, alternatively, a temperature of about 50° C. or less, and a moderate to high salt (SSPE) concentration, for example 1M NaCl.

"High stringency" conditions are well known to the skilled artisan and can comprise, for example, a temperature of about 42° C. or less, a formamide concentration of less than about 20%, and a low salt (SSC) concentration; or, alternatively, a temperature of about 65° C., or less, and a low salt (SSPE) concentration. For example, high stringency conditions comprise hybridization in 0.5 M $NaHPO_4$, 7% sodium dodecyl sulfate (SDS), 1 mM EDTA at 65° C. (See e.g. Ausubel, F. M. et al. *Current Protocols in Molecular Biology*, Vol. I, 1989; Green Inc. New York, at 2.10.3).

"SSC" comprises a hybridization and wash solution. A stock 20×SSC solution contains 3M sodium chloride, 0.3M sodium citrate, pH 7.0.

"SSPE" comprises a hybridization and wash solution. A 1×SSPE solution contains 180 mM NaCl, 9 mM $Na_2HPO_4$, 0.9 mM $NaH_2PO_4$ and 1 mM EDTA, pH 7.4.

"Substantially pure" used in reference to a peptide or protein means that said peptide or protein is separated from a large fraction of all other cellular and non-cellular molecules, including other protein molecules. A substantially pure preparation would be about at least 85% pure; preferably about at least 95% pure. For example, a "substantially pure" protein as described herein could be prepared by the IMAC protein purification method.

The term "vector" as used herein refers to a nucleic acid compound used for introducing exogenous or endogenous DNA into host cells. A vector comprises a nucleotide sequence, which may encode one or more protein molecules. Plasmids, cosmids, viruses, and bacteriophages, in the natural state or which have undergone recombinant engineering, are examples of commonly used vectors.

The nucleotide and amino acid abbreviations used herein are those accepted in the art and by the United States Patent and Trademark Office, as set forth in 37 C.F.R. 1.822 (b)(2).

Descriptions herein relating to proteolysis of FLINT and FLINT analogs between positions 218 and 219 of SEQ ID NO:1 (mature FLINT) are intended also to relate to SEQ ID NO:3 (native FLINT with leader), where the comparable region lies between positions 247 and 248.

Applicants have discovered that FLINT polypeptides are cleaved in vivo between the arginine residue at position 218 and the alanine residue at position 219 of SEQ ID NO:1, probably by a trypsin-like protease. A cleavage product of this reaction comprises residues 1–218 of SEQ ID NO:1, termed "FLINT metabolite." FLINT metabolite can be produced in vitro by treating a FLINT polypeptide with a trypsin-like protease, for example, thrombin, trypsin, or other serine protease.

One embodiment of the present invention relates to a method to produce analogs of a FLINT polypeptide that are resistant to proteolysis between positions 218 and 219 of SEQ ID NO:1 and retain biological activity. Biological activity relates to the capacity of an analog to bind FasL and/or LIGHT, and may include an inhibition of apoptosis in viva and/or in vitro.

Another embodiment of the present invention relates to analogs of a FLINT polypeptide that are resistant to proteolysis between positions 218 and 219 of SEQ ID NO:1 and retain biological activity. Biological activity relates to the capacity of an analog to bind FasL and/or LIGHT, and may include an inhibition of apoptosis in vivo and/or in vitro.

Preferred FLINT analogs provide a half-life at least 5%, 10%, 20%, 30%, 40%, or between 50% to 100% greater than FLINT, as determined by the ratio over time of full length FLINT to digestion products comprising FLINT metabolite and the carboxyl fragment (i.e. residues 219–271 of SEQ ID NO1); most preferably a FLINT analog possesses a half-life at least 2-fold to 100-fold or greater than FLINT.

FLINT analogs comprise one or more primary or secondary structural changes, for example amino acid substitutions, deletions, inversions, additions, or changes in glycosylation sites or patterns and/or combinations thereof that prevent or diminish proteolysis, and/or the rate thereof, between positions 218 and 219 of SEQ ID NO:1. Preferably these changes occur at or near the thrombin-like recognition sequence, in the case of FLINT, PTPR; most preferably, at or near the PR dipeptide sequence at positions 217 and 218 of SEQ ID NO:1. As the skilled artisan understands, residues at or near a recognition site can also affect the susceptibility of the substrate protein to proteolysis by altering the charge milieu at the active site and/or by creating alterations by steric hindrance in the region of the active site.

Therefore, the invention contemplates FLINT analogs comprising amino acid changes in FLINT, preferably in the region from about position 214 through position 222 of SEQ ID NO:1 or the comparable region of SEQ ID NO:3, wherein said analogs are resistant to proteolysis at position 218 of SEQ ID NO:1.

Also contemplated are protease-resistant FLINT analogs comprising substitutions, deletions, insertions, inversions, additions, or changes in glycosylation sites or patterns that occur outside the preferred window comprising residues 214 through 222 of SEQ ID NO:1. As the skilled artisan understands, many substitutions, and/or other changes in a protein's sequence or structure, can be made without substantially affecting the biological activity of the protein. For example, making conservative amino acid substitutions, or changing one amino acid for another from the same class of amino acids, for example negatively charged residues, positively charged residues, polar uncharged residues, and nonpolar residues, or any other classification acceptable in the art are often without effect on function. Such changes are intended to be within the scope of the present invention.

In one embodiment, a single amino acid change is made within this region; alternatively, at least two changes are made within this region; alternatively, at least three changes are made within this region; alternatively, at least four changes are made within this region.

In one embodiment, the invention relates to FLINT analog polypeptides and nucleic acids that are defined with reference to a percent identity similarity to SEQ ID NO:1, SEQ ID NO:2, and/or SEQ ID NO:3. Sequence identity refers to a comparison between two molecules using standard algorithms well known in the art. Although any suitable sequence comparison algorithm can be used for this purpose, for illustration, this embodiment shall be described with reference to the well-known Smith-Waterman algorithm using SEQ ID NO:1 as the reference sequence to define percent identity to a comparator sequence. When sequence identity is used with reference to a polypeptide, the entire polypeptide may be used in the comparison or a defined sub-region thereof.

The choice of parameter values for matches, mismatches, and inserts or deletions is arbitrary. A preferred set of values for use with the Smith-Waterman algorithm is set forth in the "maximum similarity segments" approach, which uses values of 1 for a matched residue, and −1/3 for a mismatched residue (See Waterman, Bulletin of Mathematical Biology, 46, 473–500, 1984). Insertions and deletions (indels), x, are weighted as follows:

$$X_k=1+k/3$$

Where k is the number of residues in a given insert or deletion.

For example, a comparator sequence that has 20 substitutions and 3 insertions relative to the 250 residue reference protein sequence would have an identity of:

$$[(1×250)−(1/3×20)−(1+3/3)]/250=96\%$$

identical.

FLINT analogs of the present invention can easily be tested for biological activity and/or sensitivity to proteolysis as described herein; See e.g. Examples 11 and 12. Biological activity can be assessed using either in vitro (see Example 6) or in vivo (see Example 9) models as described herein.

FLINT analogs are active in binding FasL and/or LIGHT. LIGHT, a member of the TNF family, is a membrane-bound ligand that triggers distinct biological responses. LIGHT may play a role in immune modulation, and it appears to be involved in herpes virus entry (see Zhai et al., J. Clin. Invest. 102, 1142–1151, 1998; Montgomery et al. Cell, 87, 427–436, 1996). Soluble LIGHT inhibits the proliferation of various tumor cells and appears to bind the receptors LTPR and TR2 (also referred to as herpes virus entry mediator, IWEM). LIGHT is expressed highly in activated lymphocytes and evokes immune modulation from hematopoietic cells. For example, LIGHT stimulates the secretion of IFNγ. LIGHT also induces apoptosis of tumor cells that express the LTβR and TR2/HVEM receptors. The cytotoxic effect of LIGHT, which is enhanced by IFNγ, can be blocked by addition of soluble LTβR-Fc or TR2/HVEM-Fc.

The present invention relates further to the use of FLINT analog to bind LIGHT, thereby inhibiting T cell activation. T cell activation can be chronically suppressed when advantageous, for example, following organ transplantation to prevent rejection, in the treatment of autoimmune diseases, and in treating systemic inflammatory responses.

LIGHT is produced primarily by activated T lymphocytes. When LIGHT binds to HVEM on the surface of T cells it stimulates T cell proliferation (J. A. Harrop et al. J. Biol. Chem. 273, 27548–27556, 1998).

FLINT analogs of the invention can be produced by recombinant techniques or by direct chemical synthesis. The analogs may also be produced by recombinant DNA mutagenesis techniques, well known to the skilled artisan. See. e.g. K. Struhl, "Reverse biochemistry: Methods and applications for synthesizing yeast proteins in vitro," *Meth. Enzymol.* 194, 520–535. In a preferred recombinant method, site-directed mutagenesis is used to introduce defined changes into the region 214–222 of SEQ ID NO:1 or the comparable region of SEQ ID NO:3.

FLINT analogs also include modified derivatives thereof in which one or more polyethylene glycol groups (hereinafter "PEG" groups) are bonded to the N-terminus or to amine groups or thiol groups in the amino acid side chain(s). Suitable PEG groups generally have a molecular weight between about 5000 and 20,000 atomic mass units. Procedures for preparing PEGylated polypeptides are disclosed in Mumtaz and Bachhawat, *Indian Journal of Biochemistry and Biophysics* 28:346 (1991) and Franciset al., *International Journal of Hematology* 68:1 (1998), the entire teachings of which are incorporated herein by reference.

Yet another embodiment of a FLINT analog is a molecule comprising two or more modified or unmodified FLINT analogs, e.g., a dimerized FLINT analog such as R218Q. Homodimers comprising two identical analog subunits (e.g. R218Q(2)), and heterodimers, comprising two non-identical analog subunits (e.g. R218Q/R34N, D36T, D194N, S196T, R218Q) are contemplated. Dimerization can be accomplished using the PEG polymer chain method as described in Espat et al., *Journal of Surgical Research* 59: 153 (1995), or through a C-terminal fusion to a domain that induces dimerization such as a leucine zipper, as described in O'Shea et al., *Science* 254:539 (1991). The entire teachings of Espat and O'Shea are incorporated herein by reference.

Another embodiment of the invention relates to a fusion protein comprising a FLINT analog. "Fusion protein" denotes a hybrid protein molecule not found in nature comprising a translational fusion or enzymatic fusion in which two or more different proteins or fragments thereof are covalently linked on a single polypeptide chain. Human serum albumin and the C-terminal domain of thrombopoietin are examples of proteins which could be fused with a FLINT analog. Procedures for preparing fusion proteins are disclosed in EP394,827, Tranecker et al., *Nature* 331:84 (1988) and Fares, et al., *Proc. Natl. Acad. Sci. USA* 89:4304 (1192), the entire teachings of which are incorporated herein by reference.

A FLINT analog fusion protein comprises two protein segments fused together by means of a peptide bond. The first protein segment consists of at least 6, 7, 8, 9, 10, 12, 15, 20, 25, 30, 35, 40, 50, 75, 100, 125, 150, 175, 200, 225, 250, or 275 contiguous amino acid residues of an analog of the present invention (i.e. protease resistant SEQ ID NO:1 or SEQ ID NO:3). The first protein can alternatively be a full length analog of the present invention and can be N-terminal or C-terminal.

The second protein of a FLINT analog fusion protein can be a full length protein or a protein fragment. Proteins commonly used in fusion proteins include B-galactosidase, B-glucuronidase, green fluorescent protein (GFP), thrombopoietin (TPO), glutathione-S-transferase (GST), luciferase, horseradish peroxidase, and chloramphenicol acetyltransferase (CAT). Epitope tags can be used in fusion protein constructions including histidine (His) tags, FLAG tags, influenza hemagglutinin (HA) tags, Myc tags, VSV-G tags, and thioredoxin tags. Other fusion constructions can include maltose binding protein, S-tag, Lex A DNA binding domain, GAL4 DNA binding domain fusions, and herpes simplex virus BP16 protein fusions.

The FLINT analogs of the present invention can be glycosylated or unglycosylated. A glycosylated polypeptide is modified with one or more monosaccharides or oligosaccharides. A monosaccharide is a chiral polyhydroxyalkanol or polyhydroxyalkanone which typically exists in hemiacetal form. An "oligosaccharide" is a polymer of from about 2 to about 10 monosaccharides which are generally linked by acetal bonds. One type of glycosyl group commonly found in glycosylated proteins is N-acetylneuraminic acid. A glycosylated polypeptide can be N-glycosylated and/or O-glycosylated, preferably N-glycosylated.

The term "N-glycosyled polypeptide" refers to polypeptides having one or more NXS/T motifs in which the nitrogen atom in the side chain amide of the asparagine is covalently bonded to a glycosyl group. "X" refers to any naturally occurring amino acid residue except proline. The "naturally occurring amino acids" are glycine, alanine, valine, leucine, isoleucine, proline, serine, threonine, cysteine, methionine, lysine, arganine, glutamic acid, asparatic acid, glutamine, asparagine, phenylalanine, histidine, tyrosine and tryptophan. N-Glycosylated proteins are optionally O-glycosylation.

The term "O-glycosyled polypeptide" refers to polypeptides having one or more serines and/or threonine in which the oxygen atom in the side chain is covalently bonded to a glycosyl group. O-Glycosylated proteins are optionally N-glycosylation.

Glycosylated polypeptides and analogs of the invention can be prepared recombinantly by expressing a gene encoding a polypeptide in a suitable mammalian host cell, resulting in glycosylation of side chain amides found in accessible NXT/S motifs on the polypeptide surface and of side chain alcohols of surface accessible serines and threonines. Specific procedures for recombinantly expressing genes in mammalian cells are provided hereinbelow. Other procedures for preparing glycosylated proteins are disclosed in EP 640,619 to Elliot and Burn, the entire teachings of which are incorporated herein by reference. Unglycosylated polypeptides can be prepared recombinantly by expressing a gene encoding a polypeptide in a suitable procaryotic host cell.

The present invention also relates to nucleic acids, e.g. cDNAs, DNAS, or RNAs, encoding a FLINT analog of the present invention and vectors comprising said nucleic acids. The skilled artisan understands that said nucleic acids can be prepared synthetically by mutating a nucleic acid template that encodes FLINT, e.g. introducing appropriate point mutations into a CDNA encoding FLINT using any number of suitable mutagenic techniques known to the skilled artisan to produce a protease resistant or substantially protease resistant analog of the present invention. Alternatively, said nucleic acids can be prepared synthetically de novo based on knowledge of the genetic code and the particular analog of SEQ ID NO:1 or SEQ ID NO:3 that one is interested in. Codon preference may be taken into account when designing a suitable nucleic acid.

For example, the amino acid sequences of the analogs of the present invention are described elsewhere in this application as comprising deletions, substitutions and/or additions at and around position 218 of SEQ ID NO:1, or elsewhere in the FLINT sequence. The skilled artisan understands that use of the genetic code in combination with knowledge of preferred codon usage is adequate to describe and would enable the construction of any number of nucleic acids that encode any particular analog desired. For example, the codon that encodes arginine at position 218 of SEQ ID NO:1 in native FLINT is "agg." One of the analogs of the invention changes the arginine at this position to glutamine, which may be accomplished by changing the codon from "agg" to "caa" or "cag." Choice of which codon to use for any particular amino acid may be based on knowledge of preferred codon usage and/or by trial and error considering expression of the analog. Other analogs contemplated by the invention are describable and enabled in the same manner.

A FLINT CDNA can be synthesized by RT-PCR using conventional techniques. For example, PolyA RNA is prepared from a tissue known to express the FLINT gene (e.g. human lung), using standard methods. First strand FLINT CDNA synthesis is achieved in a reverse transcriptase reaction using a FLINT sequence derived downstream primer. A commercially available kit such as GEN MP by Perkin Elmer may be employed. In a subsequent PCR, FLINT specific forward and reverse primers are used to amplify the CDNA. The amplified sample may be analyzed by agarose gel electrophoresis to check the length of the amplified fragment.

FLINT CDNA generated in this manner is used as a template for introducing appropriate point mutations (i.e. construction of FLINT analog cDNAs). A suitable protocol is described in detail in "Current Protocols in Molecular Biology", volume 1, section 8.5.7 (John Wiley and Sons, Inc. publishers), the entire teachings of which are incorporated herein by reference. Briefly, synthetic oligonucleotides are designed to incorporate one or more point mutations) at one end of an amplified fragment, e.g. at position 218 of SEQ ID NO:1. Following first strand PCR, the amplified fragments encompassing the mutation are annealed with each other and extended by mutually primed synthesis. Annealing is followed by a second PCR step utilizing 5' forward and 3' reverse end primers in which the entire mutagenized fragment gets amplified and is ready for subdloning into the appropriate vector.

The skilled artisan understands that the degeneracy of the genetic code provides multiple codons in some instances for a given amino acid. All such nucleic acid sequence variants are intended to be within the scope of the invention.

Using the information provided herein, such as the amino acid sequence of SEQ ID NO:1 or SEQ ID NO:3, or the nucleotide sequence of SEQ ID NO:2 or variants thereof, a nucleic acid molecule of the present invention encoding a FLINT analog can be obtained using well-known methods.

Nucleic acid molecules of the present invention can be in the form of RNA, such as mRNA, hnRNA, or any other form, or in the form of DNA, including, but not limited to, CDNA and genomic DNA obtained by cloning or produced synthetically, or any combination thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

The present invention further provides isolated nucleic acids that encode a protease resistant FLINT analog and that hybridize under selective conditions to a polynucleotide disclosed and/or contemplated herein, e.g., SEQ ID NO:2 and/or derivatives thereof.

The present invention further provides isolated nucleic acids comprising FLINT analog polynucleotides, wherein the polynucleotides are complementary to the polynucleotides of the invention. Complementary sequences base-pair throughout the entirety of their length with such polynucleotides (i.e., have 100% sequence identity over their entire length). Complementary bases associate through hydrogen bonding in double-stranded nucleic acids. For example, the following base pairs are complementary: guanine and cytosine; adenine and thymine; and adenine and uracil. (See, e.g., Ausubel, supra; or Sambrook, supra)

Construction of Nucleic Acids

The isolated nucleic acids of the present invention can be made using (a) standard recombinant methods, (b) synthetic techniques, (c) purification techniques, or combinations thereof, as well known in the art.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. For example, a hexa-histidine marker sequence provides a convenient means to purify the proteins of the present invention.

Recombinant Methods for Constructing Nucleic Acids

The isolated nucleic acid compositions of this invention, such as RNA, cDNA, genomic DNA, or a hybrid thereof, can be obtained from biological sources using any number of cloning methodologies known to those of skill in the art. In some embodiments, oligonucleotide probes which selectively hybridize, under stringent conditions, to the polynucleotides of the present invention are used to identify the desired sequence in a CDNA or genomic DNA library. Isolation of RNA and construction of cDNA and genomic libraries is well known to those of ordinary skill in the art. (See, e.g., Ausubel, supra; or Sambrook, supra)

Nucleic Acid Screening and Isolation Methods

A cDNA or genomic library can be screened using a probe based upon the sequence of a polynucleotide of the present invention, such as those disclosed herein. Probes may be used to hybridize with genomic DNA or CDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%; however, it should be understood that minor sequence variations in the probes and primers may be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification.processes (see, e.g., U.S. Pat. Nos. U.S. Pat. Nos. 4,683,195, 4,683,202, 4,800,159, 4,965,188, to Mullis, et al.; U.S. Pat. Nos. 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification which uses anti-sense RNA to the target sequence as a template for double-stranded DNA synthesis (U.S. Pat. No. 5,130,238 to Malek, et al, with the tradename NASBA), the entire contents of which are herein incorporated by reference. (See, e.g., Ausubel, supra; or Sambrook, supra)

For instance, polymerase chain reaction (PCR) technology can be used to amplify the sequences of polynucleotides of the present invention and related genes directly from genomic DNA, cDNA libraries, or cloned DNA or RNA. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, Sambrook, and Ausubel, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

Synthetic Methods for Constructing Nucleic Acids

The isolated nucleic acids of the present invention can also be prepared by direct chemical synthesis by methods such as the phosphotriester method of Narang, et al., Meth. Enzymol. 68:90–99 (1979); the phosphodiester method of Brown, et al., Meth. Enzymol. 68:109–151 (1979); the diethylphosphoramidite method of Beaucage, et al., Tetra. Letts. 22:1859–1862 (1981); the solid phase phosphoramidite triester method described by Beaucage and Caruthers, Tetra. Letts. 22(20):1859–1862 (1981), e.g., using an automated synthesizer, e.g., as described in Needham-VanDevanter, et al., Nucleic Acids Res. 12:6159–6168 (1984); and the solid support method of U.S. Pat. No. 4,458,066. Chemical synthesis generally produces a single-stranded oligonucleotide, which may be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences may be obtained by the ligation of shorter sequences.

The present invention also relates to vectors that include isolated nucleic acid molecules of the present invention, host cells that are genetically engineered with the recombinant vectors, and production of FLINT analogs, as is well known in the art. (See, e.g., Sambrook, et al., 1989; Ausubel, et al., 1987–1998, which is entirely incorporated herein by reference).

"Vector" refers to a nucleic acid compound used for introducing exogenous or endogenous nucleic acid into host cells. A vector comprises a polydeoxynucleotide sequence which encodes a FLINT analog or fusion protein thereof. Plasmids, cosmids, viruses and bacteriophages, in a natural state or which have undergone recombinant engineering, are non-limiting examples of commonly used vectors to provide recombinant vectors comprising at least one desired isolated nucleic acid molecule.

"Host cell" refers to any eucaryotic, procaryotic, or other cell or pseudo cell or membrane-containing construct that is suitable for propagating and/or expressing an isolated nucleic acid that is introduced into a host cell by any suitable means known in the art (e.g., transformation or transfection, or the like), or induced to express an endogenous polydeoxynucleic acid. The cell can be part of a tissue or organism, isolated in culture or in any other suitable form.

The nucleic acids of the invention, including cDNAs, can optionally be joined to a vector containing a selectable marker for propagation in a host. Generally, a plasmid vector is introduced in a precipitate, such as a calcium phosphate precipitate, or in a complex with a charged lipid (e.g., lipofectamine). If the vector is a virus, it can be packaged in vitro using an appropriate packaging cell line and then transduced into host cells.

The DNA insert may be operatively linked to an appropriate promoter, such as the phage lambda PL promoter, phage T7 promoter, the E. coli lac, tzp and tac promoters, the SV40 early and late promoters and promoters of retroviral LTRs, or any other suitable promoter. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UGA and UAA preferred for mammalian or eucaryotic cell expression.

Expression vectors will preferably include at least one selectable marker. Such markers include, e.g., dihydrofolate reductase, neomycin, zeocin, hygromycin B or puromycin resistance for eucaryotic cell culture, and kanamycin or ampicillin resistance genes for culturing in E. coli and other bacteria or procaryotics. Representative examples of appropriate hosts include, but are not limited to, bacterial cells, such as *E. coli, Streptomyces, Bacullus subtilis* and *Salmonella typhimurium* cells; yeast cells such as *Saccharomyces cervisiae, Saccharomyces pombe* or *Pichia pastoris*; insect cells such as *Drosophila* S2, *Spodoptera* Sf9 cells or Sf21 and High Five (BTI-TN-5B1-4) cells; animal cells such as 293, 293EBNA, CHO, COS and COS7, BHK, AV12, 3T3, HeLa, and Bowes melanoma cells; and plant cells. Appropriate culture mediums and conditions for the above-described host cells are known in the art. Vectors preferred for use in bacteria include pET15 and pET30 available from Novagen, pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKR223-3, pKK233-3, pDR540, pRIT5 available from Pharmacia. Preferred eucaryotic vectors include pWLNEO, pSV2CAT, pOG44, pXT1 and pSG available from Stratagene; pSVK3, pBPV, pMSG and pSVL available from Pharmacia, and the commonly used vector pcDNA3.1 available from Invitrogen. Other suitable vectors will be readily apparent to the skilled artisan.

Introduction of a vector construct into a host cell can be effected by calcium phosphate transfection, DRAE-dextran mediated transfection, cationic lipid-mediated transfection, electroporation, transduction, infection or other methods. Such methods are described in many standard laboratory manuals, such as Sambrook, supra, Chapters 1–4 and 16–18; Ausubel, supra, Chapters 1, 9, 13, 15, 16, the entire relevant teachings of which are incorporated herein by reference.

Another aspect of the present invention relates to fusion proteins comprising FLINT analogs. For instance, a region of additional amino acids, for example hexahistidine ($His_6$) tag, can be added to the amino or carboxy terminus of a FLINT analog to facilitate purification. Such regions can be removed prior to final purification of an analog if desired. Such methods are described in many standard laboratory manuals, such as Sambrook, supra, Chapters 17.29–17.42 and 18.1–18.74; Ausubel, supra, Chapters 16, 17 and 18, the entire relevant teachings of which are incorporated herein by reference.

Expression of FLINT Analogs in Host Cells

Using the nucleic acids of the present invention, one may express a FLINT analog in a recombinantly engineered cell, such as bacteria, yeast, insect, or mammalian cells.

Those of skill in the art are knowledgeable in the numerous expression systems available for expression of a nucleic acid encoding a FLINT analog of the present invention. No attempt to describe in detail the various methods known for the expression of proteins in procaryotes or eucaryotes will be made.

Briefly, the expression of isolated nucleic acids encoding a FLINT analog of the present invention will typically be achieved by operably linking a DNA or cDNA encoding an analog to a promoter (which is either constitutive or inducible), followed by incorporation into an expression vector. The vectors can be suitable for replication and integration in either procaryotes or eucaryotes. Typical expression vectors contain transcription and translation terminators, initiation sequences and promoters useful for regulation of the expression of the DNA encoding a protein of the present invention. To obtain high level expression of a cloned gene, it is desirable to construct expression vectors which contain, at the minimum, a promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification handle sequences.

Expression in Procaryotes

Procaryotic cells may be used as hosts for expression of FLINT analog(s). Procaryotes most frequently are represented by various strains of *E. coli*; however, other microbial strains may also be used. commonly used procaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., Nature 198:1056 (1977)), the tryptophan (trp) promoter system (Goeddel, et al., Nucleic Acids Res. 8:4057 (1980)), T7 phage promoter (Studier, F. W., Methods in Enzymology, 185, 60–89, (1990),and the lambda derived PL promoter and N-gene ribosome binding site (Shimatake, et al., Nature 292:128 (1981)), the teachings of which are incorporated herein by reference. The inclusion of selection markers in DNA vectors transfected in *E. coli* is also useful. Examples of such markers include genes specifying resistance to ampicillin, tetracycline, chloramphenicol or kanamycin.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transformed with the plasmid vector DNA. Expression systems for expressing a protein of the present invention are available using *Bacillus subtilis* and *Salmonella* (Palva, et al., Gene 22:229–235 (1983); Mosbach, et al., Nature 302:543–545 (1983)), the teachings of which are incorporated herein by reference.

Expression in Eucaryotes

A variety of eucaryotic expression systems such as yeast, insect cell lines, plant and mammalian cells, are known to those of skill in the art. As explained below, a nucleic acid encoding a FLINT analog of the present invention can be expressed in these eucaryotic systems.

Synthesis of heterologous proteins in yeast is well known. F. Sherman, et al., Methods in Yeast Genetics, Cold Spring Harbor Laboratory (1982), the teachings of which are incorporated herein by reference, is a well-recognized work describing the various methods available to produce the protein in yeast. Two widely utilized yeast for production of eucaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A FLINT analog of the present invention expressed in yeast can be isolated by standard protein isolation techniques. Monitoring the purification process can be accomplished by using SDS polyacrylamide gel electrophoresis (SDS-PAGE), Western blot techniques or radioimmunoassay of other standard immunoassay techniques such as ELISA. can be expressed in these eucaryotic systems.

The nucleic acid sequences encoding FLINT analogs of the present invention can also be ligated to various expression vectors for use in transfecting cell cultures of, for instance, mammalian, insect, or plant origin. Illustrative of cell cultures useful for the production of the peptides are mamalian cells. Mammalian cell systems often will be in the form of monolayers of cells although mammalian cell suspensions may also be used. A number of suitable host cell lines capable of expressing intact proteins have been developed in the art, and include the AV12, HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., Immunol. Rev. 89:49 (1986), the entire teachings of which are incorporated herein by reference), and processing information sites, such as ribosome binding sites, RNA splice sites, polyadenylation sites (e.g., bovine growth hormone poly A addition site), and transcriptional terminator sequences. Other animal cells useful for production of proteins of the present invention are available, for instance, from the American Type Culture Collection Catalogue of Cell Lines and Hybridomas (8th edition, 1994).

Appropriate vectors for expressing a FLINT analog of the present invention in insect cells are usually derived from the SF9 baculovirus. Suitable insect cell lines include mosquito larvae, silkworm, armyworm, moth and *Drosophila* cell lines such as a Schneider cell line (See Schneider, J. Embryol. Exp. Morphol. 27:353–365 (1987), the entire teachings of which are incorporated herein by reference.

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., J. Virol. 45:773–781 (1983), the entire teachings of which are incorporated herein by reference). Additionally, gene sequences to control replication in the host cell may be incorporated into the vector such as those found in bovine papilloma virus type-vectors. M. Saveria-Campo, Bovine Papilloma Virus DNA, a Eucaryotic Cloning Vector in DNA Cloning Vol. II, a Practical Approach, D. M. Glover, Ed., IRL Press, Arlington, Va., pp. 213–238 (1985), the entire teachings of which are incorporated herein by reference.

Protein Purification

A FLINT analog of the present invention can be recovered and purified from recombinant cells that express an analog (e.g, *E. coli*, yeast, insect, or mammalian cell cultures) by well-known methods including ammonium sulfate or ethanol precipitation, acid extraction, anion or cation exchange chromatography including immobilized metal ion chelating peptide technology, "IMAC," as taught in U.S. Pat. No. 4,569,974 herein incorporated by reference, phosphocellulose chromatography, hydrophobic interaction chromatography, affinity chromatography, hydroxylapatite chromatography and lectin chromatography. Most preferably, high performance liquid chromatography ("HPLC") is employed for purification.

Analogs of the present invention can be produced by chemical synthetic procedures, or by recombinant techniques from a procaryotic or eucaryotic host, including bacterial, yeast, higher plant, insect and mammalian cells. Such methods are described in many standard laboratory manuals, such as Sambrook, supra, Chapters 17.37–17.42; Ausubel, supra, Chapters 10, 12, 13, 16, 18 and 20, the entire relevant teachings of which are incorporated herein by reference. Depending upon the host employed, the polypeptides of the present invention may be glycosylated or non-glycosylated. In addition, polypeptides of the invention can also include an initial modified methionine residue, in some cases as a result of host-mediated processes.

Therapeutic Applications

The apoptosis-triggering molecule, FasL, is an important homeostatic regulator of the immune system, triggering autoreactive peripheral T cell deletion and dampening the cell-mediated immune response (i.e. activation-induced cell death). FasL also appears to be an important apoptotic stimulus in non-immune cells under certain conditions (e.g., inflammation). FasL exists in two forms: membrane-bound and secreted. The latter is derived from proteolytic cleavage and probably plays an additional role in inflammation by attracting neutrophils. FLINT binds both forms of FasL, inhibiting FasL interactions with the membrane-bound Fas receptor and with LIGHT, a secreted activator of T cells and possibly also a trigger for certain cancer cells to die by apoptosis. Constitutive cell surface expression of FasL on certain tissues conveys immune privilege status, such that cell-mediated immunity does not occur or occurs weakly (due to destruction of invading immune cells bearing Fas on their surface). FasL expression is probably regulated in all other tissues; Pas and Pas pathway inhibitors (e.g., FLIP, FAIM) are also highly regulated.

Following are some of the factors and/or conditions that regulate FasL expression in humans: inflammation (e.g., acute lung injury), carcinogenesis (e.g., melanoma, colon carcinoma), viral infection (e.g., Hepatitis C, HIV), autoimmune triggers (e.g., ulcerative colitis, Hashimoto's thyroiditis), and ischemia/re-perfusion (e.g., spinal cord injury). Undoubtedly many other regulators of FasL expression exist, and it is likely that FasL expression and secretion can be induced in any tissue under certain conditions.

The clinical utility for FLINT analogs is expected to be substantial. Many diseases and/or conditions involving FasL/Fas are potentially amenable to therapy with FLINT analog. Examples of suitable diseases and/or conditions include:

Inflammatory/autoimmune diseases—Rheumatoid arthritis, inflammatory bowel disease, graft-versus-host disease, insulin-dependent diabetes, SIRS/sepsis/MODS, pancreatitis, psoriasis, multiple sclerosis, Hashimoto's thyroiditis, Gravels disease, transplant rejection, SLE, autoimmune gastritis, fibrosing lung disease.

Infectious diseases—HIV-induced lymphopenia, fulminant viral hepatitis B/C, chronic hepatitis/cirrhosis, H. pylori-associated ulceration.

Ischemia/Re-perfusion conditions—Acute coronary syndrome, acute myocardial infarction, congestive heart failure, atherosclerosis, acute cerebral ischemia/infarction, brain/spinal cord trauma, organ preservation during transplant Other—Cytoprotection during cancer treatment, adjuvant to chemotherapy, Alzheimer's, chronic glomerulonephritis, osteoporosis, TTP/HUS, aplastic anemia, myelodysplasia. Also of interest are treatment and prevention of acute lung injury (ALI)/acute respiratory distress syndrome (ARDS); Ulcerative colitis; and Crohn's disease.

FLINT analogs inhibit the binding of FAS to FASL and LIGHT to LTβR and TR2/HVEM receptors, and can be used to treat or prevent a disease and/or condition that may be associated with such binding.

Runaway apoptosis is one example of a condition caused by excessive activation of the PAS/FASL signal transduction pathway that can be treated with the FLINT analogs of the present invention (see U.S. Provisional Application Serial No. 60/112,577, filed Dec. 18, 1998, Kondo et al., Nature Medicine 3(4):409–413 (1997) and Galle et al., *J. Exp. Med.* 182:1223–1230 (1995), the entire teachings of which are incorporated herein by reference). Runaway apoptosis leads to multiple pathological conditions including organ failure, acute liver failure (e.g., liver failure associated with viral infections affecting the liver, bacterial infections affecting the liver, hepatitis, hepatocellular injury and/or other conditions where hepatocytes undergo massive apoptosis or destruction), kidney failure, and failure of pancreatic function.

The FLINT analogs of the present invention are generally clinically and/or therapeutically useful for diseases which can be treated with FLINT. (See U.S. patent application Ser. No. 09/280,567; and Miwa et al., *Nature Medicine* 4:1287 (1998), the entire teachings of which are incorporated herein by reference). One example is inflammation caused by FASL induced neutrophil activation. Inflammatory disease associated with neutrophil activation includes sepsis, ARDS, SIRS and MODS.

Other diseases for which FLINT analog is therapeutically useful include Rbeumatoid arthritis (Elliott et al., *Lancet* 344:1105–10 (1994)), fibroproliferative lung disease, fibrotic lung disease, HIV (Dockrell et al., *J. Clin. Invest.* 101:2394–2405 (1998)), Ischemia (Sakurai et al. 1998 Brain Res 797:23–28), Brain trauma/injury (Ertel et al. 1997 J Neuroimmunol 80:93–6), chronic renal failure (Schelling et al. 1998 Lab Invest 78:813–824), Graft-vs-Host Disease (GVHD) (Hattori et al. 1998 Blood 11:4051–4055), Cutaneous inflammation (Orteu at al. 1998 J Immunol 161:1619–1629), Vascular leak syndrome (Rafi et al. 1998 J Immunol 161:3077–3086), *Helicobacter pylori* infection (Rudi et al. 1998 J Clin Invest 102:1506–1514), Goiter (Tamura et al. 1998 Endocrinology 139:3646–3653), Atherosclerosis (Sata and Walsh, 1998 J Clin Invest 102:1682–1689), IDDM (Itoh et al. 1997 J Exp Med 186:613–618), Osteoporosis (Jilka et al. 1998 J Bone Min Res 13:793–802), Crohn's Disease (van Dullemen et al. 1995 Gastroenterology 109:129–35), organ preservation and transplant (graft) rejection (Lau et al. 1996 Science 273:109–112), Sepsis (Faist and Kim. 1998 New Horizons 6:S97–102), Pancreatitis (Neoptolemos et al. 1998 Gut 42:886–91), Cancer (melanoma, colon and esophageal) (Bennett et al. 1998 J Immunol 160:5669–5675), Autoimmune disease (IBD, psoriasis, Down's Syndrome (Seidi et al., *Neuroscience Lett.* 260:9 (1999) and multiple sclerosis (D'Souza et al. 1996 J Exp Med 184:2361–70).

Co-pending U.S. patent application, Ser. No. 09/280567, entitled "Therapeutic Applications of mFLINT Polypeptides," filed Mar. 30, 1999, herein incorporated by reference, discloses other diseases which can be treated with FLINT analog. Examples include Alzheimer's Disease; End-stage renal disease (ESRD); mononulceosis; EBV; Herpes; antibody dependent sytotoxicity; hemolytic and hypercoagulation disorders such as vascular bleeds, DIC (disseminated intervascular coagulation), eclampsia, HELLP (preeclampsia complicated by thrombocytopenia, hemolysis and disturbed liver function), HITS (heparin induced thromobcytopenia), HUS (hemolytic uremic syndrome), and preeclampsia; hematopoeitic disorders such as aplastic anemia, thrombocytopenia (TTP) and myelodysplasia; and hemolytic fever caused, for example, by *E.bola*.

In the case of organ preservation in preparation for harvesting, for instance, FLINT analog is useful prophylactically to prevent the apoptosis associated with ischemia reperfusion injury to the organ once it is removed from the donor. In one embodiment of this aspect of the invention, FLINT analog is administered to the organ donor prior to harvesting the organ. After harvesting the organ, FLINT analog is added to a suitable medium for transport/storage of the organ. Alternatively, the harvested organ is perfused with a medium containing FLINT analog prior to transplantation into a recipient. Suitable media for this purpose are known, for example, the media disclosed in EP 0356367 A2, herein incorporated by reference. The method may also include treating the transplant recipient with FLINT analog prior to and/or after the transplant surgery.

A typical method involves pre-treating the organ donor with an effective amount of FLINT analog prior to organ harvesting. Alternatively, or conjunctively, the harvested organ may be perfused or bathed in a FLINT analog-containing solution. This method may be employed, for example, with kidney, heart, lung and other organs and tissues.

The ability of FLINT analogs to retard apoptosis under ischemic conditions is useful for preserving organs and tissues harvested for transplantation. Ischemic conditions include, but are not limited to, neuronal ischemia, limb crush injuries, spinal cord injuries, myocardial infarct including acute, subacute and chronic sequelae and related clinical syndromes, congestive heart failure. Also, innocent bystander tissues which are damaged during chemotherapy, radiation therapy, toxic drugs, trauma, surgery and other stresses can be treated with FLINT analog. One example of such a disease is mucositis which can be a life-threatening side-effect of cancer treatment.

In another embodiment, therefore, the invention relates to administering FLINT analog to an organ donor prior to harvesting an organ. After organ harvesting, FLINT analog is added to a suitable medium for transport and/or storage of the organ. Alternatively, the harvested organ is perfused with a medium containing FLINT analog prior to transplantation into a recipient. Suitable media for perfusion are known, for example, the medium disclosed in EP 0356367 A2. The method may also include treating the transplant recipient with FLINT analog prior to and/or after the transplant surgery.

In this aspect, an organ donor is pre-treated with an effective amount of FLINT analog prior to organ harvesting. Alternatively, or conjunctively, the harvested organ may be perfused or bathed in a solution containing FLINT analog. The method may be employed, for example, with kidney, heart, lung and other organs and tissues.

Acute Lung Injury and Acute Respiratory Distress Syndrome

Acute lung injury (ALI) and acute respiratory distress syndrome (ARDS) represent disease entities that differ only in the severity of the hypoxemia present at diagnosis. A widely accepted parameter for diagnosis is the PaO2 to FiO2 ratio, according to which ARDS patients manifest a ratio of less than or equal to 200 mm Hg, whereas ALI patients exhibit values of less than or equal to 300 mm Hg. ARDS represents a more severe form of ALI. Numerous mediators are likely to contribute to the pathogenesis of ARDS/ALI with neutrophils playing a prominent role. While multiple precipitating factors are probable in the development of ARDS, both direct and indirect, the major cause appears to be sepsis and the systemic inflammatory response syndrome, accounting for approximately 40% of cases. Mortality in ARDS is high approximating 40%, with most deaths occurring within the first 2 to 3 weeks. There is no currently available, approved pharmacologic therapy for ARDS and treatment at present is limited to aggressive supportive care.

There is evidence that ARDS may be mediated by soluble FasL/Pas interaction in humans (Matute-Bello et al., J. Immunol. 163, 2217–2225, 1999). FLINT analog, by binding to FasL, could inhibit FasL-mediated apoptosis of pneumocytes and/or endothelial cells, thus inhibiting or preventing the progression from acute inflammatory insult to ALI, and from ALI to ARDS.

Therefore, in another embodiment, the present invention relates to the use of FLINT analog to inhibit and/or treat ALI and/or ARDS comprising the administration of a therapeutically effective amount of FLINT analog to a person in need thereof.

Chronic Obstructive Pulmonary Disease (COPD)

Chronic obstructive pulmonary disease (COPD) is the fourth leading cause of non-accidental death in the United States following heart disease, cancer and cerebral vascular disease. COPD is an obstructive airway disorder encompassing multiple conditions including chronic bronchitis, emphysema, bronchiectasis, and chronic asthma. COPD is slowly progressive and produces an irreversible decline in lung function. Chronic hypoxemia and hypercapnia are the eventual outcomes of the disorder. The mechanism by which COPD disrupts lung function appears to involve dysregulated apoptosis. Plasma samples from patients suffering from COPD exhibit higher concentrations of soluble Fas compared with healthy control subjects (See Yasuda et al. Resp. Med. 92, 993–999, 1998). The increased levels of soluble Fas in COPD patients may reflect increased Fas-induced apoptosis.

In another embodiment, the present invention relates to the use of FLINT analog to treat and/or inhibit COPD in a patient in need thereof by administering a therapeutically effective amount of FLINT analog.

Pulmonary Fibrosis (PF)

Pulmonary fibrosis (also known as fibrosing lung disease) occurs as an end result of the process of attempted healing during acute or chronic lung injury. The pathological mechanism of such lung injury can be any of various factors that first trigger an inflammatory response in the alveoli or surrounding interstitium and subsequently trigger alveolar/interstitial fibrosis (i.e. the repair response). Fibrosis in other tissues such as the epidermis or the peritoneum, leads to visible scarring or adhesions, respectively. Pulmonary fibrosis, in contrast, leads to restrictive lung disease (decreased lung capacities and decreaased oxygen diffusion). Conditions associated with pulmonary fibrosis include but are not limited to: idiopathic pulmonary fibrosis, connective tissue diseases (e.g. lupus, scleroderma), drug-induced lung disease (e.g. bleomycin), pneumoconioses (e.g. asbestosis), sarcoidosis, eosinophilic granulomatosis, hypersensitivity pneumonitis, and other diseases asscoiated with severe lung inflammation that can result in acute lung injury and/or acute respiratory distress syndrome (e.g. trauma, sepsis, near-drowning, gastric aspiration, shock, etc.). Fibrosis of the airways is also a feature of the chronic inflammation in COPD.

The etiology of PF may involve FasL/Fas-triggered apoptosis. Indeed, an intact FasLiFas system is essential in the etiology of bleomycin-induced PF in mice (See Kuwano K. et al. J. Clin. Invest. 104, 13–19 (1999).

In another embodiment the present invention relates to the use of FLINT analog to inhibit and/or treat PF. For example, FLINT analog can be administered acutely at the time of an inflammatory insult to the lung (e.g. during bleomycin treatment) to prevent PF from occurring.

A "subject" is a mammal in need of treatment, preferably a human, but can also be an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like).

An "effective amount" of a FLINT analog is an amount which results in a sufficient inhibition of one or more processes mediated by the binding of FAS to FAS Ligand or LIGHT to LTβR and/or TR2/HVEM so as to achieve a desired therapeutic or prophylactic effect in a subject with a disease or condition associated with aberrant FAS/FAS Ligand binding and/or LIGHT mediated binding. One example of such a process is runaway apoptosis. Alternatively, an "effective amount" of a FLINT analog is a quantity sufficient to achieve a desired therapeutic and/or prophylactic effect in a subject with inflammation caused by FAS Ligand induced neutrophil activation or any of the other aforementioned diseases associated with aberrant FAS Ligand activity.

A "desired therapeutic and/or prophylactic effect" in a subject with a disease or condition includes the amelioration of symptoms, or delay in onset of symptoms, associated with such disease. Alternatively, a "desired therapeutic and/or prophylactic effect" includes an increased survival rate or increased longevity for the subject with the disease.

The amount of FLINT analog administered to the individual will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors.

As a general proposition, the total pharmaceutically effective amount of the FLINT analogs of the present invention administered parenterally per dose will be in the range of about 1 μg/kg/day to 10 mg/kg/day of patient body weight, particularly 2 mg/kg/day to 8 mg/kg/day, more particularly 2 mg/kg/day to 4 mg/kg/day, even more particularly 2.2 mg/kg/day to 3.3 mg/kg/day, and finally 2.5 mg/kg/day, although, as noted above, this will be subject to therapeutic discretion. More preferably, this dose is at least 0.01 mg/kg/day. If given continuously, the FLINT analogs of the present invention are typically administered at a dose rate of about 1 μg/kg/hour to about 50 μg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the FLINT analogs of the present invention may be administered orally, rectally, intracranially, parenterally, intracisternally, intravaginally, intraperitoneally, topically (as by powders, ointments, drops or transdermal patch), transdermally, intrathecally, bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein includes, but is not limited to, modes of administration which include intravenous, intramuscular, intraperitoneal, intrasternal, subcutaneous and intraarticular injection, infusion and implants comprising FLINT analogs.

The FLINT analogs of the present invention are also suitably administered by sustained-release systems. Suitable examples of sustained-release compositions include semipermeable polymer matrices in the form of shaped articles, e.g., films, or microcapsules. Sustained-release matrices include polylactides (U.S. Pat. No. 3,773.919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R.Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(–)-3-hydroxybutyric acid (EP 133,988). Other sustained-release compositions also include liposomally entrapped FLINT analog. Such liposomes are prepared by methods known per se: DE 3,218,121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EDP 143,949; EP 142,641; Japanese Pat. Appl. 83-118008; U.S. Pat. Nos. 4,485,045 and 4,544,545; and EP 102,324. ordinarily, the liposomes are of the small (about 200–800 Angstroms) unilamellar type in which the lipid content is greater than about 30 mol. percent cholesterol, the selected proportion being adjusted for the optimal TNFR polypeptide therapy.

For parenteral administration, the FLINT analogs of the present invention are formulated generally by mixing at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the FLINT analogs of the present invention uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The FLINT analogs of the present invention are typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of salts of the FLINT analogs of the present invention.

Polypeptides to be used for therapeutic administration must be sterile. Sterility is readily accomplished by filtration through sterile filtration membranes (e.g., 0.2 micron membranes). Therapeutic polypeptide compositions generally are placed into a container having a sterile access port. for example, an intravenous solution bag or vial having a stopper pierceable by a hypodermic injection needle.

FLINT analogs ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution of one of the FLINT analogs of the present invention, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such containers) can be a notice in the form prescribed by a governmental agency regulating the manufacture, use or sale of pharmaceuticals or biological products, which notice reflects approval by the agency of manufacture, use or sale for human administration. In addition, the FLINT analogs of the present invention may be employed in conjunction with other therapeutical compounds.

The invention is illustrated by the following examples which are not intended to be limiting in any way.

EXAMPLE 1

Production of a Vector for Expressing FLINT Analog R218Q

FLINT variant R218Q was constructed by mutagenic PCR starting from a wild-type FLINT template. See e.g. Saiki R. K. et al. *Science* 239:487–491 (1988), and "Current Protocols in Molecular Biology", Vol 1, section 8.5.7 (John Wiley and Sons, Inc. publishers) the entire contents of which are herein incorporated by reference. The R218Q mutant substitutes an arginine residue found at amino acid 218 with glutamine.

The mutagenic PCR process utilized a SOEing reaction (i.e. Strand Overlap Extension) to create specific mutations in the native FLINT template for the purpose of changing the amino acid sequence at position 218, and further for introducing restriction enzyme tags for identification purposes.

Generally, SOEing reactions require the use of four primers, two in the forward orientation (termed A, SEQ ID NO:5, and C, SEQ ID NO:7) and two in the reverse orientation (termed B, SEQ ID NO:6 and D, SEQ ID NO:8). The SOEing reaction amplifies a nucleic acid sequence (e.g. gene sequence) in two stages. The first step is to amplify "half" the gene by performing an A to B reaction followed by a separate C to D reaction. In constructing the R218Q mutant, the B and C primers were targeted to the same area of the gene but on opposite strands. Mismatch priming from both oligonucleotide primers institutes the mutation. After these two reactions were completed, the products were isolated and mixed for use as the template for the A to D reaction, which yields the desired mutated product.

The primers involved in the cloning of R218Q were:

```
Primer A:  CF 107   (39 nt)
GCACCAGGGTACCAGGAGCTGAGGAGTGTGAGCGTGCCG

Primer B:  CF 111   (44 nt)
TCAGCTGCAAGGCGGCGCGCCCCGCTTGTGGTGTCGGACCCCAG

Primer C:  CF 112   (44 nt)
GGGGTCCGACACCACAAGCGGGGCGCGCCGCCTTGCAGCTGAAG

Primer D:  CF 110   (43 nt)
GCACAGAATTCATCAGTGCACAGGGAGGAAGCGCTCACGGACG
```

The nucleotides shown in bold represent changes made to the wild type sequence. Using the forward primer C as a reference, the bold G and C show the silent changes necessary to introduced an AscI site. This recognition site is underlined in primers B and C. The bold CAA shows the amino acid substitution of glutamine (CAA) for arginine (AGG).

The 311 base pair amplified fragment carrying the R218Q mutation was sub-cloned using a 51 KpnI site (GGTACC) and a 3' EcoRI site (GAATTC). The native FLINT sequence has a naturally occurring internal KpnI site around amino acid position 176. The EcoRI site was introduced for sub-cloning purposes and lies downstream of the stop codons. These sites are underlined in primers A and D respectively. The 311 bp fragment was incorporated into the full length FLINT sequence. This was accomplished through the following steps:

I. The 311 bp fragment was placed into an intermediate vector, pCR2.1-TOPO, which utilizes the adenine overhangs established after PCR for ligation.

II. Once incorporated, a KpnI to EcoRI digestion removed a 289 bp fragment. (Note: the size of the PCR fragment decreased from 311 bp to 289 bp due to the digestion). The mutated fragment was used to replace the corresponding segment in the wild type FLINT gene by directional ligation.

III. FLINT/pJB03 was digested with KpnI to EcoRI to produce two fragments

Fragment 1: 6070 bp

Fragment 2: 289 bp

IV. The 6070 bp fragment carrying the FLINT gene was isolated and ligated with the 289 bp PCR product removed from the pCR 2.1-TOPO vector to create R218Q/pJB03. Positive clones were identified by restriction digestion and subsequently confirmed by sequence analysis.

The R218Q analog contained in R218Q/pJB03 was shuffled into the pIG3 vector by means of a NheI to XbaI undirected ligation. R218Q/pJB03 was digested with NheI to XbaI to yield fragments of 932 and 5427 bp. The 932 bp FLINT R218Q containing fragment was isolated. The 932 bp NheI and XbaI fragment of R218Q was ligated with the 8510 bp linearized pIG 3 vector to generate clones in both forward and inverse orientations.

EXAMPLE 2

Procaryotic Expression and Purification of Recombinant FLINT Analogs

An expression vector that carries an open reading frame (ORF) encoding FLINT analog R218Q is transformed into competent *E. coli* strain BL21 (DE3)(hsdS gal cIts857 ind1Sam7nin5lacUV5-T7gene 1)available from Novagen (Madison Wis.) using standard methods. Multiple transformants, selected for resistance to kanamycin, were chosen at random and used to inoculate LB/kanamycin media. Cultures were grown at 37° C. with shaking to cell density of $OD_{600}$=0.8–1.0 at which point FLINT protein synthesis was induced with 1 mM IPTG. Cultures were grown at 37° C. for 3h postinduction before the cells are harvested. FLINT analog product encoded by the vector-borne ORF was purified from the insoluble fraction of cell lysate, the inclusion bodies. In brief, the purification consisted of inclusion bodies preparation and solubilization, and protein refolding followed by cation-exchange and size-exclusion chromatography procedures, respectively.

EXAMPLE 3

Construction of Vector pIG3 for Expression of FLINT Analogs in Mammalian Cells A bicistronic expression vector is constructed by insertion into the mammalian expression vector PGTD (Gerlitz, B. et al., 1993, Biochemical Journal 295:131) a PCR fragment encoding an "internal ribosome entry site"/enhanced green fluorescent polypeptide (IRES/eGFP). This new vector, designated pIG3, contains the following sequence landmarks: the Ela-responsive GBMT promoter (D. T. Berg et al., 1993 BioTechniques 14:972; D.T. Berg et al., 1992 Nucleic Acids Research 20:5485); a multiple cloning site (MCS); the IRES sequence from encephalomyocarditis virus (EMCV); the eGFP coding sequence (Cormack, et al., 1996 Gene 173:33, Clontech); the SV40 small "t" antigen splice site/polyadenylation sequences; the SV40 early promoter and origin of replication; the murine dihydrofolate reductase (dhfr) coding sequence; and the ampicillin. resistance gene and origin of replication from pBR322.

Based on the human FLINT cDNA sequence, the forward and reverse PCR primers are synthesized bearing BclI restriction sites at their respective 5'ends. These primers are used to PCR amplify the FLINT analog CDNA. The human FLINT cDNA orientation and nucleotide sequence are confirmed by restriction digest and double stranded sequencing of the insert. The approximately 900 base pair amplified FLINT analog PCR product was digested with restriction endonucleases NheI and XbaI, respectively, to generate a fragment bearing NheI and XbaI sticky ends. This fragment was subsequently ligated into a unique XbaI site of pIG3 to generate recombinant plasmid pIG3-FLINT. The insert encoding the analog can be modified at the C-terminus of the analog to introduce a cleavable hexahistidine (His6) cassette to facilitate analog purification.

EXAMPLE 4

Isolation of High-Producing FLINT Analog Clone from AV12 RGT18 Transfectants The recombinant plasmid carrying the FLINT gene encodes resistance to methotrexate. In addition, the construct contains a gene encoding a fluorescent polypeptide, GFP, on the same transcript and immediately 3' to the FLINT gene. Since high level expression of GFP would require a high level of expression of the FLINT-GFP mRNA, highly fluorescent clones would have a greater probability of producing high levels of FLINT.

AV12 RGT18 cells are transfected using a calcium phosphate procedure with recombinant pIG1 plasmids containing FLINT analogs. Cells resistant to 250 nM methotrexate are selected and pooled. The pool of resistant clones is subjected to fluorescence assisted cell sorting (FACS), and cells having fluorescence values in the top 5% of the population are sorted into a pool and as single cells. High fluorescence pools are subjected to two successive sorting cycles. Pools and individual clones from the first and second cycles are analyzed for FLINT analog production by ELISA. Pools or clones expressing FLINT analog at the highest level are used for scale-up and FLINT analog purification.

EXAMPLE 5

Quantitation of FLINT Analogs

FLINT analogs can be quantitated in crude media of transfected cells and during purification procedure by developed FLINT ELISA. ELISA uses anti-FLINT polyclonal antibody TKD-028(1494) as a capture antibody and biotinylated anti-FLINT TKD-076A as a primary antibody in a "sandwich" assay. ELISA is developed by streptavidin derivatized horse radish peroxidase (SA-HRP) using OPD as a substrate and monitoring the absorbance at 490 mn. The useful range of such an ELISA is from 0.2–20 ng/ml.

EXAMPLE 6

FLINT Analogs Inhibit FasL Induced Jurkat Cell Apoptosis

A bioassay measuring the prevention of apoptosis (i.e. cell survival) was performed using FLINT and a variety of FLINT analogs produced in mammalian cell culture. For this purpose, 25 µl of Jurkat cells ($5 \times 10^4$ cells/well) were added to each well of a 96-well plate and mixed with 25 µl of recombinant human FasL (final concentration 150 ng/ml), and either 50 µl of FLINT or FLINT analog. serial dilutions ranging from 0 to 1 mg/ml were tested in the assay. Cells were incubated at 37° C. over night. Twenty µl of MTS tetrazolium compound (Promega Corporation, Madison, Wis.) was added to each well and the incubation carried out for 2h at 37° C. Absorbance at 490 nm was recorded using a plate reader.

The results are summarized in the Table below and in FIGS. 2-4. Analogs that changed arginine at position 218 to glutamine, glutamic acid, alanine, glycine, or valine showed activity in this assay. Bioactivity was not a function of the cell type from which the sample was prepared. For example, R218Q purified from AV12 cells (FIG. 2), or from 293 EDNA cells (FIG. 3) were active in the assay.

Other analogs were also tested. For example, a double mutant analog that replaced threonine at position 216 with proline, and arginine at position 218 with glutamine, was active in the assay. Also active was the multi-substituted analog [R34N, D36T, D194N, S196T, R218Q] analog was active in this assay (FIG. 4).

| FLINT/FLINT ANALOG | INHIBITION OF JURKAT CELL APOPTOSIS |
|---|---|
| FLINT | ++ |
| R218Q | ++ |
| R218A | + |
| R218G | + |
| R218V | + |
| P217Y | + |
| R34N, D36T, R218Q | + |
| R218E | ++ |
| R34N, D36T, D194N, S196T, R218Q | + |
| T216P, R218Q | ++ |

EXAMPLE 7

Testing FLINT Analogs for Inhibition of Apoptosis of Jurkat Cells Induced by FasL A bioassay measuring the prevention of apoptosis (i.e. cell survival) is performed using FLINT and a variety of FLINT analogs (see Table below) produced in mammalian cell culture. FLINT analogs to be tested include: G214(1), G214(2), G214(3), G214(4), G214(5); P215(1), P215(2), P215(3), P215(4), P215(5); T216(1), T216(2), T216(3), T216(4), T216(5); P217(1), P217(2), P217(3), P217(4), P217(5); R218(1), R218(2), R218(3), R218(4), R218(5); A219(1), A219(2), A219(3), A219(4), A219(5); G220(1), G220(2), G220(3), G220(4), G220(5); R221(1), R221(2), R221(3), R221(4), R221(5); A222(1), A222(2), A222(3), A22(4), A222(5). Parenthetical numbers designate specific amino acid subgroups as follows with the proviso that the replacement residue not be the same as that in native FLINT:

(1) any of the natural 20 amino acids;
(2) Asp or Glu
(3) His, Arg, or Lys
(4) Cys, Thr, Ser. Gly, Asn, Gln, Tyr
(5) Ala, Pro, Met, Leu, Ile, Val, Phe, Trp For this purpose, 25 $\mu$l of Jurkat cells ($5\times10^4$ cells/well) are added to each well of a 96-well plate and mixed with 25 $\mu$l of recombinant human FasL (final concentration 150ng/ml), and either 50 $\mu$l of FLINT or a FLINT analog. Serial dilutions ranging from 0 to 1 mg/ml are tested in the assay. Cells are incubated at 37° C. over night. Twenty $\mu$l of MTS tetrazolium compound (Promega Corporation, Madison, Wis.) is added to each well and the incubation carried out for 2h at 37° C. Absorbance at 490 nm is recorded using a plate reader.

| TESTING REPRESENTATIVE FLINT ANALOGS FOR BIOLOGICAL ACTIVITY |
|---|
| G214D, G214H, G214T, G214A |
| P215D, P215H, P215T, P215A |
| T216D, T216H, T216S, T216A |
| P217D, P217H, P217T, P217A |
| A219D, A219H, A219T, A219M |
| G220D, G220H, G220T, G220A |
| R221D, R221H, R221T, R221A |
| A222D, A222H, A222T, A222M |

EXAMPLE 8

Large Scale FLINT Analog Polypeptide Purification

Large scale production of FLINT analog (containing a 6 histidine tag) is performed by growing stable pools in roller bottles. After reaching confluency, cells are further incubated in serum-free medium for 5 to 7 days to secrete maximum amounts of FLINT analog into the medium. Medium that contains FLINT analog is concentrated in an Amicon ProFlux M12 tangential filtration system to 350 ml. The concentrated medium is passed over an IMAC column (Immobilized Metal-Affinity Chromatography(Pharmacia, 5 to 10 ml column) at a flow rate of 1 ml/min. The column is washed with buffer A(PBS, 0.5 M NaCl, pH 7.4) until the absorbency (280 nm) returned to baseline and the bound polypeptide is eluted with a linear gradient from 0.025 M-0.5 M Imidazol(in buffer A) developed over 60 min. Fractions containing the FLINT analog are pooled. This material is passed over a Benzamidine Sepharose column(1 to 5 ml) to remove the thrombin at a flow rate of 1 ml/min. The column flow-through containing the FLINT analog is concentrated using an Ultrafree centrifugal filter unit (Millipore) to 2 ml. This material is passed over a 16/60 Superdex 200 sizing column (Pharmacia)equilibrated with PBS, 0.5 M NaCl, pH 7.4. Fractions containing the FLINT analog are analyzed by SDS-PAGE, and the N-terminal sequence of the purified polypeptide confirmed to be FLINT.

EXAMPLE 9

Biophysical Characterization of Purified FLINT Analogs

The structural integrity and physical and chemical stability of FLINT analogs are characterized as follows.

Structural analysis of proteins includes assessment of secondary structure normally obtained by far-UV CD analysis. Usually 100 µl of 1 mg/ml FLINT analog in phosphate buffer, pH 7.4 is used to scan from 240–180 nm in 0.5 nm steps, 1 nm bandwidth, with 3 sec time constant, an average of 3 scans in a 0.01 cm cell at room temperature. Near-UV CD spectra reporting information on the tertiary structure is taken from 240–350 nm, 0.5 nm step, 1 nm bandwidth, 5 second time constant, with average of 3 scans at room temperature.

Intrinsic tryptophan fluorescence is measured with the following parameters: excitation through a 1 cm pathlength cell at 298 nm with a 2/2 nm slit width with emission collected from 305–400 nm with a 2/2 nm slit width, 05 nm step, through a 0.4 cm pathlength with 1 sec integration time. A "blue shift" is generally indicative that aromatic residues are more deeply buried in the protein structure and is often accompanied by improved pharmaceutical properties.

Quaternary structure of FLINT analogs can be examined by equilibrium sedimentation analysis performed in an ultracentrifuge with 3 mm width cells. Analogs with similar equilibrium sedimentation values compared to native FLINT are preferred.

Physical stability analysis includes examination of the propensity for aggregation of FLINT analogs as a reflection of their surface properties. Physical stability assays are described in the following paragraphs.

Dynamic Light Scattering Assay(DLS): A FLINT analog solution is diluted into either a) PBS, pH 7.4 or b) PBS, 0.5 M NaCl or c) PBS, pH 7.4 and 3 mg/mL m-Cresol, containing 0.1 to 5 mg/mL protein. The pH is adjusted to 7.4 (±0.05) with HCl/NaOH and filtered into a 6×50 mm borasilica type-I glass tube. The average light-scatter intensity weighted particle size is collected on a Brookhaven BI900 Instrument consisting of a goniometer at a 90° angle, digital correlator, and a Lexel model 3500 argon ion laser adjusted to the 488-nm line. The experimentally determined autocorrelation function C(t) is analyzed by the cumulants method to yield the hydrodynamic diameter. The time before a significant change in particle size, or lag time, is determined by fitting linear lines to the pre-growth and growth phase data points. The intersection is defined as the lag time. Decreased light scattering by an analog compared with native FLINT at the same concentration and temperature is generally indicative that the analog aggregates to a lesser extent than native protein.

Differential Scanning Callorimetry (DSC): Physical stability is also reflected in the melting temperature (Tm) of the protein by DSC (Differential Scanning Callorimetry). Usually FLINT analogs are scanned from 5°–100° C. with a 60° C./h scan rate and a 16 second filtering parameter. Higher melting temperatures are generally indicative of physical stability.

Chemical stability of FLINT analogs diluted to 0.5 mg/ml is monitored by analyses by reversed-phase HPLC (RP-HPLC) and size exclusion chromatography. The reversed-phase method consists of an acetonitrile/TFA gradient systems optimized for FLINT with detection at 214 nm using a Zorbax 300SB-C8 column at 40° C. The size exclusion method consists of a PBS mobile phase at pH 7.4 on a Superdex-75 (3.2×300mm) column at room temperature. Changes in the reverse-phase chromatogram are generally indicative of chemical instability.

EXAMPLE 10

In vivo Testing of FLINT Analogs for Treatment of Liver Damage

Liver damage was induced in vivo in a mouse model using the method of Tsuji H., et al, 1997, *Infection and Immunity*, 65(5):1892–1898. Mice were challenged with a low dose of lipopolysaccaride (LPS) to induce acute and massive hepatic injury. The ability of FLINT and FLINT analogs to protect against acute inflammation and apoptosis was determined. Briefly, BALB/c mice (Harlan) were given intravenous injections (the lateral tail vein) of 6 mg of D(+)-Galactosamine (Sigma, 39F-0539) in 100 µl of PBS (GIBCO-BRL) and 3 µg of Lipopolysaccharide B *E.coli* 026:B6 (LPS) (Difco, 3920-25-2) in 100 µl of PBS. After LPS challenge, the animals were injected intravenously with FLINT (1–200 µg) or a FLINT analog (1–200 µg), at 4 hour after LPS treatment. The survival rates of the mice were determined after 48 hours (see FIG. 7).

A correlation was observed in the percent survival of animals and the amount of FLINT or analog administered. In one study, involving 5 animals per test group, analogs R218Q, and [R34N, D36T, D194N, S196T, R218Q] protected animals from liver damage in a dose dependent fashion (see FIG. 7). In a second experiment, involving 10 animals per test group, 7 of 10 animals survived at 20 hours post-treatment with FLINT, R218Q, and [R34N, D36T, D194N, S196T, R218Q]. At 24 hours post-treatment, 7 of 10 animals survived with FLINT treatment, and 6 of 10 survived with R218Q or [R34N, D36T, D194N, S196T, R218Q].

EXAMPLE 11

FLINT Analog/FAS Ligand Binding Assay

The binding between FLINT analogs and Fas Ligand can be confirmed and the binding properties determined (e.g., kinetics, specificity, affinity, cooperativity, relative binding pattern) using real-time biomolecular interaction analysis (hereinafter BIA). To monitor biomolecular interactions, BIA uses optical phenomenon surface plasmon resonance. Detection of binding interactions depends on changes in the mass concentration of macromolecules at the biospecific interface. The following materials and methods were used.
Biacore® 2000 device (Biacore AB, Rapsgatan 7, S-754 50 Uppsala, Sweden)
Sensor Chip CM5 (Biacore)
Amine coupling kit (Biacore)
Washing buffer: HBS-EP (Biacore)
Guanidine Isothiocyanate Solution (GibcoBRL)
Fas Ligand (Kamiya Biomedical Company, 910 Industry Drive, Seattle, Wash. 98188)
FLINT Analogs
Pas/Fc chimera (R&D Systems)

Immobilization Protocol:

FasL or the FLINT analog are immobilized through their primary amine group on lysine residues onto carboxymethyldextran polymer attached to a gold surface (Sensor Chip CM5). Immobilization is carried out using the amine coupling kit (Biacore) according to the manufacturer's protocol. Briefly, 100 µl of either FasL or FLINT analog solutions (10–25 µg/ml in sodium acetate buffer 20 mM, pH 5.0) is loaded onto an activated CM5 chip. After coupling, excess reactive groups on the surface are deactivated with 1M ethanolamine hydrochloride pH 8.5. The chip is then washed with a sodium acetate buffer 20 mM, pH 5.0 to remove non-covalently bound material.

Interaction Analysis:

To analyze the interaction between FasL and FLINT analogs, solutions containing the FLINT analogs are passed over the chip with PasL immobilized thereon. The amount of the FLINT analog associated with FasL is determined by measuring the surface plasmon resonance signal (in responce units, RU). Typically, FLINT analog solutions at different concentrations in HBS-ET buffer are loaded on the sensor chip for 10 minutes at a flow rate of 5 µl/min. The chip is then washed with HBS-ET buffer (10 mM Hepes, pH 7.4; 150 mM NaCl, 3 mM EDTA, 0.005% Surfactant P20) for 2 minutes at a flow rate of 5 µl/min. The bioactive surface of the chip is then regenerated by exposure to 0.8 M guanidine isothiocyanate for 2 minutes at a flow rate of 5 µl/min and then HBS-EP buffer for 2 minutes at 5 µl/min flow rate.

The converse reaction can also be done whereby a FasL solution is passed over a chip having FLINT analog immobilized thereon. The amount of FasL associated with the FLINT analog is determined using surface plasmon resonance signal (in response units, RU).

Determination of Affinity Constants:

The data is evaluated and binding parameters determined using BIA evaluation 3.0.2 software (Biacore). The Kd for the interaction between FLINT and FasL and between FasL and Fas was determined using the protocols described above. The results are shown below:

Interacting molecules:
Immobilized—in solution
 Kd (nM)
FasLigand (monomer)—FLINT
 $1.13 \times 10^{-7}$
FasLigand (monomer)—Fas
 $1.62 \times 10^{-7}$
FLINT analog—FasLigand (trimer)
 $0.63 \times 10^{31\ 9}$

EXAMPLE 12

Analytical Thrombin Digestion of FLINT and FLINT Analogs

In separate reaction tubes, 1 ug of FLINT and 1 ug of the FLINT analogs R218Q, ER34N, D36T), and [R34N, D36T, D194N, S196T, R218Q] were incubated in a buffer containing 20 mM Tris, 150 mM NaCl, pH 7.4 or PBS, 0.5 M NaCl, 10% glycerol and thrombin at a weight ratio of 1 to 100 (thrombin to FLINT/analog). The reaction mixtures were incubated for varying times at either 25 °C. or 37° C. Aliquots from the reaction mixtures were analyzed by SDS-PAGE to detect cleavage at position 218. The results are presented in FIG. 1. As expected, FLINT was digested by thrombin to produce the FLINT metabolite. For example, by 50 min. almost half the FLINT and a control analog [R34N, D36T] were proteolized and at 4 hr. >90% was proteolized. In contrast, proteolysis at the 218 position was not detected on samples of the R218Q and [R34N, D36T, D194N, S196T, R218Q] analogs even out to the 4 hour time point (FIG. 1).

EXAMPLE 13

Metabolic Stability In vitro of FLINT Analog R218Q

FLINT derived from AV12 cells was supplied as a solution of 0.16 mg/ml in phosphate buffered saline/0.5 M NaCl/10% glycerol. FLINT analog(R218Q), derived from 293 EBNA cells, was supplied as a solution of 0.12 mg/ml in phosphate buffered saline/0.5 M NaCl/10% glycerol. Materials were stored at 4° C. until use. FLINT and FLINT analog (R218Q) were radiolabeled with $^{125}$I-NaI using the IODO-BEADS iodination reagent (PIERCE). Radiolabeled test articles were >90% precipitable in trichloroacetic acid. Radiolabeled proteins were stored at −20° C. until use.

For in vitro analysis, mouse blood samples were collected by cardiac puncture into clotting tubes (serum tubes, no anti-coagulant) from male ICR mice (weighing 35 g to 45 g). Immediately thereafter, $^{125}$I-FLINT or $^{125}$I-FLINT analog (R218Q) was added to the blood collection tubes. The tubes were then placed in a water bath at 37° C. and allowed to clot for 1 hr. Serum was prepared by sedimentation and assayed by reversed-phase HPLC.

Figure 5B:
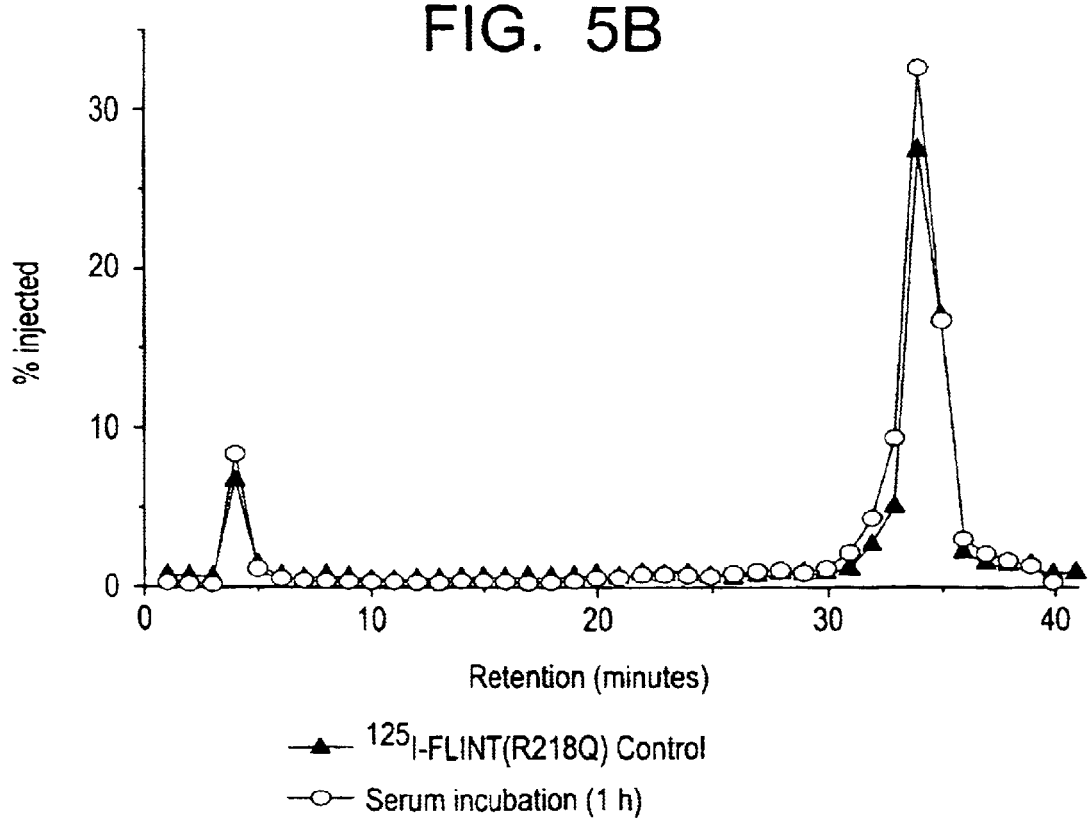

Serum or plasma samples were applied directly to a Vydac C4 Column (4.6×250 MM). Compound(s) were eluted from the column with a linear gradient of 15–55% B in 40 min at 1 ml/min. Solvent A=$H_2O$/0.1% TFA; solvent B=acetonitrile/0.08% TFA. Eluate was monitored at 214 nm. Fractions of column eluate (1 ml) were collected. Radioactivity in fractions was analyzed directly by gamma counting. In vitro incubation. After a 1 h incubation with ICR mouse blood, approximately 75% of $^{125}$I-FLINT was degraded to a product having the retention characteristics of the FLINT metabolite, (i.e. residues 1–218 of SEQ ID NO:1). (FIG. 5A) In contrast, the FLINT analog (R218Q) was completely resistant to proteolytic degradation (FIG. 5B).

EXAMPLE 14

Metabolic Stability in vivo of FLINT Analog R218Q

Studies designed to test the stability and resistance of FLINT analog. to proteolytic digestion in vivo were performed in male ICR mice (bdywt. 35 g–45g). FLINT and FLINT analog (R218Q) were diluted in phosphate buffered saline/10% glycerol to give dose solutions having a final concentration of 75 µg/ml. FLINT and FLINT analog (R21SQ) were administered to ICR mice (n=2) as a single intravenous bolus via the tail vein (15 µg/animal) in a volume of 0.2 ml. At 0.25 h after intravenous administration of test articles, blood samples were collected by cardiac puncture into EDTA tubes containing 0.01 ml of a protease inhibitor cocktail (0.5 mM AEBSF, 150 rM aprotinin, 1 µm E-64, 1 µM leupeptin) and plasma prepared by sedimentation. Plasma concentrations of FLINT or FLINT analog (R218Q) were determined by ELISA and the metabolic profile of FLINT immuoreactivity was determined using reversed-phase HPLC as described below.

FLINT ELISA: Wells of a 96-well microtiter plate were coated overnight with purified polyclonal antibody TKD-028-1494 (5 µg/ml, 0.1 ml/well). After washing, samples were added in a volume of 50 µl/well and incubated at room temperature for 2 h. After washing, biotinylated Ab TKD-076A was added (1:4000 dilution, 50 µl/well) and incubated at room temperature for 1 h. After washing, streptavidin-alkaline phosphatase (Boehringer Ingleheim) was added (1:1000 dilution, 50 µl/well) and incubated at room temperature for 1 h. Detection was accomplished with Attophos™ substrate, 50 µl/well. Fluorescence intensity was measured at 15 minute intervals at room temperature in a Biolumin. The LOQ of the assay was determined to be approximately 0.5 ng/ml.

The ELISA analysis showed that plasma concentrations of FLINT and PLINT analog (R218Q) were comparable (approximately 200–300 ng/ml) when measured 15 minutes after intravenous administration. However, in order to distinguish between full length FLINT and metabolic FLINT (i.e. residues 1–218 of SEQ ID NO:1) RP-HLPC was carried out. Collected fractions were concentrated to dryness in a Speed-Vac (Savant Instruments), resuspended in PBS/0.1% BSA and assayed by ELISA.

Figure 6A:
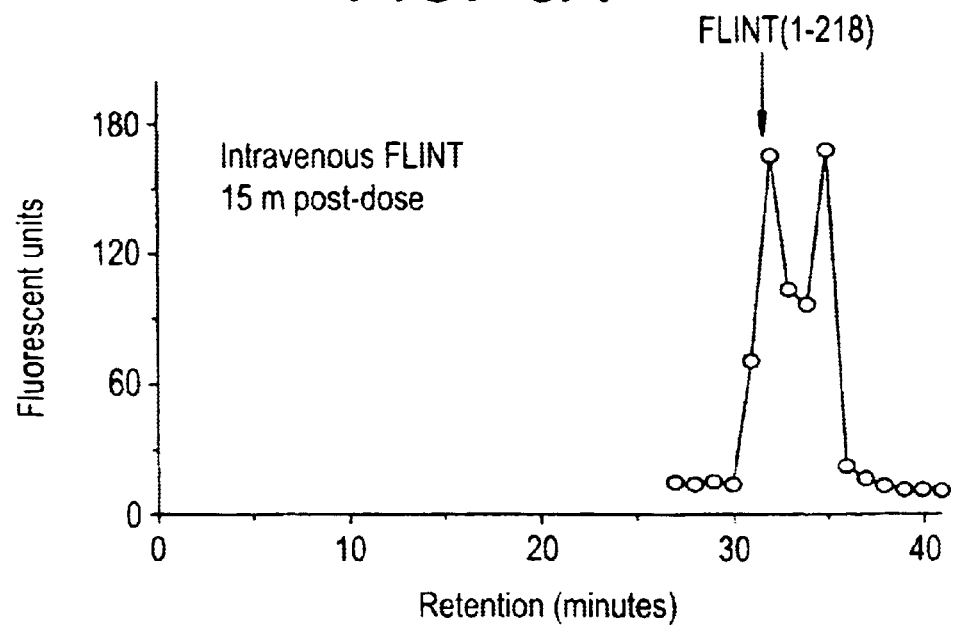
Figure 6B:
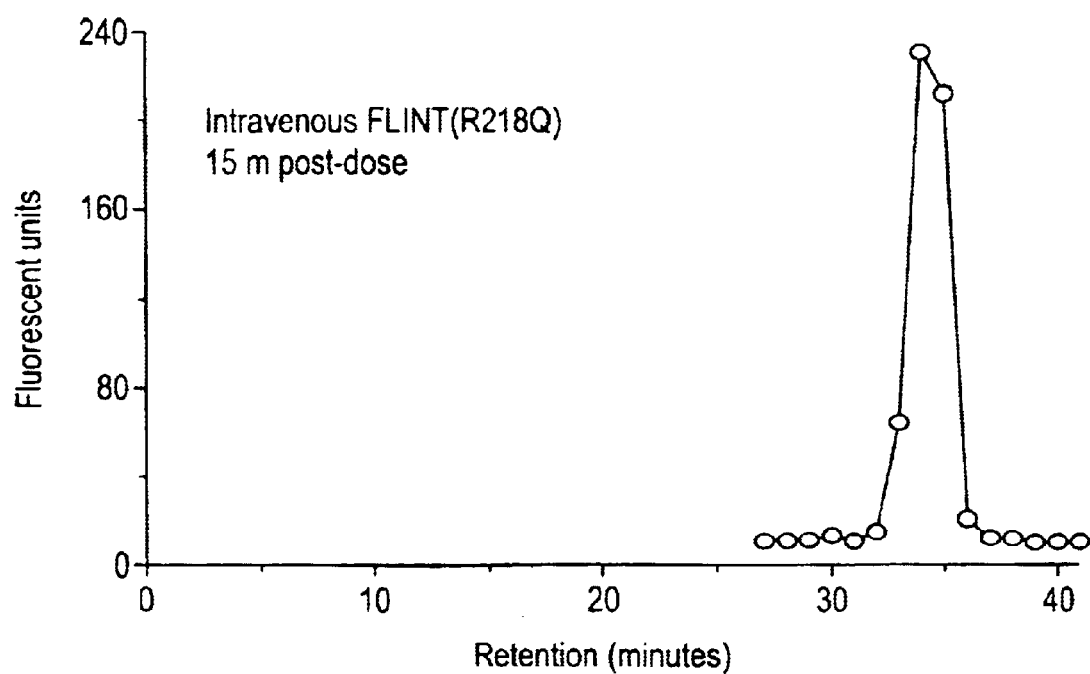

RP-HPLC fractionation indicated that FLINT metabolite (1–218) represented approximately 50% of the circulating immunoreactivity 15 minutes after intravenous administration of native FLINT (FIG. 6A). In contrast, FLINT metabolite was not observed in the plasma from animals administered FLINT analog (R218Q). Essentially all immunoreactivity was accounted for solely by the FLINT analog(R218Q), indicating resistance to proteolytic degradation at the R218Q position (FIG. 6B).

EXAMPLE 15

Use of FLINT Analog to Treat ALI Patient

A 55 year-old male presents to the emergency department unconscious. His family states that he was being treated as an outpatient for bronchitis for the past few days but worsened despite antibiotics. He has no relevant past history and his only medication was a third generation oral cephalosporin. Physical examination reveals an obtunded, cyanotic male who is hypotensive, tachypneic, and tachycardic, and who has bilateral lung congestion consistent with pulmonary edema. There is no evidence of congestive heart failure. Tests reveal hypoxemia (based on PaO2/FiO2) and bilateral lung infiltrates without cardiomegaly, consistent with a diagnosis of acute lung injury. Based on the history it is concluded that the lung injury was a direct result of community-acquired pneumonia, and that the patient met the hypoxemia criteria for ALI within the last 12 hours. Ventilation measures include use of PEEP and low tidal volume. As soon as adequate oxygenation is confirmed, treatment with FLINT analog R218Q is initiated in the ER as an iv bolus of 2.5 mg/kg, followed by a continuous infusion of 0.1 mg/minute. FLINT analog along with aggressive supportive measures (e.g., positive ventilation, intravenous fluids, pressors, and nutritional support) are continued for four days in the ICU, at which time the FLINT analog is discontinued. Over the following 3 days, the patient begins to recover and is extubated on Day 8. He has an uneventful recovery and 6 months following discharge has no evidence of residual lung disease by blood gas and spirometry.

EQUIVALENTS

Those skilled in the art will be able to recognize, or be able to ascertain, using no more than routine experimentation, many equivalents to the specific embodiments of the invention described herein. Such equivalents are intended to be encompassed by the following claims.

---

What is claimed is:

1. A FLINT analog resistant to proteolysis at position 218 of SEQ ID NO:1 comprising the priority of SEQ ID NO:1, with the exception that the residue of position 218 is a substitution selected from the group consisting of:
   a. Arg at position 218 is replaced by Gln
   b. Arg at position 218 is replaced by Glu;
   c. Arg at position 218 is replaced by Ala;
   d. Arg at position 218 is replaced by Gly;
   e. Arg at position 218 is replaced by Ser;
   f. Arg at position 218 is replaced by Val;
   g. Arg at position 218 is replaced by Tyr, and
   h. Arg at position 218 is replaced by Asn.

2. A FLINT analog wherein Thr at position 216 of SEQ ID NO:1 is replaced by Pro, and Arg at position 218 is replaced by Gln.

3. A method to treat or prevent a disease or condition in a mammal comprising the administration of a therapeutically effective amount of a protease resistant FLINT analog of claim 1 or claim 2.

4. A method as in claim 3 wherein said disease or condition is acute lung injury, acute respiratory distress syndrome, or ulcerative colitis.

5. A pharmaceutical formulation comprising as an active ingredient a protease resistant FLINT analog of claim 1 or claim 2 associated with one or more pharmaceutically acceptable carriers, excipients, or diluents thereof.

6. A FLINT analog resistant to proteolysis at position 218 of SEQ ID NO:1 comprising the amino acid sequence of SEQ ID NO:1, wherein Arg at position 218 is substituted by Gln.

* * * * *

SEQUENCE LISTING

```
<160> NUMBER OF SEQ ID NOS: 9

<210> SEQ ID NO 1
<211> LENGTH: 271
<212> TYPE: PRT
<213> ORGANISM: Homo sapiens

<400> SEQUENCE: 1

Val Ala Glu Thr Pro Thr Tyr Pro Trp Arg Asp Ala Glu Thr Gly Glu
 1               5                  10                  15

Arg Leu Val Cys Ala Gln Cys Pro Pro Gly Thr Phe Val Gln Arg Pro
             20                  25                  30

Cys Arg Arg Asp Ser Pro Thr Thr Cys Gly Pro Cys Pro Pro Arg His
         35                  40                  45

Tyr Thr Gln Phe Trp Asn Tyr Leu Glu Arg Cys Arg Tyr Cys Asn Val
     50                  55                  60

Leu Cys Gly Glu Arg Glu Glu Ala Arg Ala Cys His Ala Thr His
 65                  70                  75                  80

Asn Arg Ala Cys Arg Cys Arg Thr Gly Phe Phe Ala His Ala Gly Phe
                 85                  90                  95

Cys Leu Glu His Ala Ser Cys Pro Pro Gly Ala Gly Val Ile Ala Pro
            100                 105                 110

Gly Thr Pro Ser Gln Asn Thr Gln Cys Gln Pro Cys Pro Pro Gly Thr
        115                 120                 125
```

```
Phe Ser Ala Ser Ser Ser Ser Glu Gln Cys Gln Pro His Arg Asn
    130                 135                 140
Cys Thr Ala Leu Gly Leu Ala Leu Asn Val Pro Gly Ser Ser His
145                 150                 155                 160
Asp Thr Leu Cys Thr Ser Cys Thr Gly Phe Pro Leu Ser Thr Arg Val
                165                 170                 175
Pro Gly Ala Glu Glu Cys Glu Arg Ala Val Ile Asp Phe Val Ala Phe
                180                 185                 190
Gln Asp Ile Ser Ile Lys Arg Leu Gln Arg Leu Leu Gln Ala Leu Glu
                195                 200                 205
Ala Pro Glu Gly Trp Gly Pro Thr Pro Arg Ala Gly Arg Ala Ala Leu
    210                 215                 220
Gln Leu Lys Leu Arg Arg Leu Thr Glu Leu Leu Gly Ala Gln Asp
225                 230                 235                 240
Gly Ala Leu Leu Val Arg Leu Leu Gln Ala Leu Arg Val Ala Arg Met
                245                 250                 255
Pro Gly Leu Glu Arg Ser Val Arg Glu Arg Phe Leu Pro Val His
                260                 265                 270
```

<210> SEQ ID NO 2
<211> LENGTH: 813
<212> TYPE: DNA
<213> ORGANISM: Homo sapiens

<400> SEQUENCE: 2

```
gtggcagaaa cacccaccta cccctggcgg gacgcagaga caggggagcg gctggtgtgc    60
gcccagtgcc ccccaggcac ctttgtgcag cggccgtgcc gccgagacag ccccacgacg   120
tgtggcccgt gtccaccgcg ccactacacg cagttctgga actacctgga gcgctgccgc   180
tactgcaacg tcctctgcgg ggagcgtgag gaggaggcac gggcttgcca cgccacccac   240
aaccgtgcct gccgctgccg caccggcttc ttcgcgcacg ctggtttctg cttggagcac   300
gcatcgtgtc cacctggtgc cggcgtgatt gccccgggca cccccagcca gaacacgcag   360
tgccagccgt gccccccagg caccttctca gccagcagct ccagctcaga gcagtgccag   420
ccccaccgca actgcacggc cctgggcctg gccctcaatg tgccaggctc ttcctcccat   480
gacaccctgt gcaccagctg cactggcttc ccctcagca ccagggtacc aggagctgag   540
gagtgtgagc gtgccgtcat cgactttgtg gctttccagg acatctccat caagaggctg   600
cagcggctgc tgcaggccct cgaggccccg gagggctggg gtccgacacc aagggcgggc   660
cgcgcggcct tgcagctgaa gctgcgtcgg cggctcacgg agctcctggg ggcgcaggac   720
ggggcgctgc tggtgcggct gctgcaggcg ctgcgcgtgg ccaggatgcc cgggctggag   780
cggagcgtcc gtgagcgctt cctccctgtg cac                                 813
```

<210> SEQ ID NO 3
<211> LENGTH: 300
<212> TYPE: PRT
<213> ORGANISM: Homo sapiens

<400> SEQUENCE: 3

```
Met Arg Ala Leu Glu Gly Pro Gly Leu Ser Leu Leu Cys Leu Val Leu
  1               5                  10                  15
Ala Leu Pro Ala Leu Leu Pro Val Pro Ala Val Arg Gly Val Ala Glu
                 20                  25                  30
Thr Pro Thr Tyr Pro Trp Arg Asp Ala Glu Thr Gly Glu Arg Leu Val
```

```
                35                  40                  45
Cys Ala Gln Cys Pro Pro Gly Thr Phe Val Gln Arg Pro Cys Arg Arg
         50                  55                  60
Asp Ser Pro Thr Thr Cys Gly Pro Cys Pro Pro Arg His Tyr Thr Gln
 65                  70                  75                  80
Phe Trp Asn Tyr Leu Glu Arg Cys Arg Tyr Cys Asn Val Leu Cys Gly
                 85                  90                  95
Glu Arg Glu Glu Glu Ala Arg Ala Cys His Ala Thr His Asn Arg Ala
            100                 105                 110
Cys Arg Cys Arg Thr Gly Phe Phe Ala His Ala Gly Phe Cys Leu Glu
        115                 120                 125
His Ala Ser Cys Pro Pro Gly Ala Gly Val Ile Ala Pro Gly Thr Pro
    130                 135                 140
Ser Gln Asn Thr Gln Cys Gln Pro Cys Pro Pro Gly Thr Phe Ser Ala
145                 150                 155                 160
Ser Ser Ser Ser Ser Glu Gln Cys Gln Pro His Arg Asn Cys Thr Ala
                165                 170                 175
Leu Gly Leu Ala Leu Asn Val Pro Gly Ser Ser Ser His Asp Thr Leu
            180                 185                 190
Cys Thr Ser Cys Thr Gly Phe Pro Leu Ser Thr Arg Val Pro Gly Ala
        195                 200                 205
Glu Glu Cys Glu Arg Ala Val Ile Asp Phe Val Ala Phe Gln Asp Ile
    210                 215                 220
Ser Ile Lys Arg Leu Gln Arg Leu Leu Gln Ala Leu Glu Ala Pro Glu
225                 230                 235                 240
Gly Trp Gly Pro Thr Pro Arg Ala Gly Arg Ala Ala Leu Gln Leu Lys
                245                 250                 255
Leu Arg Arg Arg Leu Thr Glu Leu Leu Gly Ala Gln Asp Gly Ala Leu
            260                 265                 270
Leu Val Arg Leu Leu Gln Ala Leu Arg Val Ala Arg Met Pro Gly Leu
        275                 280                 285
Glu Arg Ser Val Arg Glu Arg Phe Leu Pro Val His
    290                 295                 300

<210> SEQ ID NO 4
<211> LENGTH: 29
<212> TYPE: PRT
<213> ORGANISM: Homo sapiens

<400> SEQUENCE: 4

Met Arg Ala Leu Glu Gly Pro Gly Leu Ser Leu Leu Cys Leu Val Leu
 1               5                  10                  15
Ala Leu Pro Ala Leu Leu Pro Val Pro Ala Val Arg Gly
            20                  25

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: oligo
      primer

<400> SEQUENCE: 5
gcaccagggt accaggagct gaggagtgtg agcgtgccg                         39

<210> SEQ ID NO 6
```

```
<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: oligo
      primer

<400> SEQUENCE: 6
tcagctgcaa ggcggcgcgc cccgcttgtg gtgtcggacc ccag                      44

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence: oligo
      primer

<400> SEQUENCE: 7
ggggtccgac accacaagcg gggcgcgccg ccttgcagct gaag                      44

<210> SEQ ID NO 8
<211> LENGTH: 43
<212> TYPE: DNA
<213> ORGANISM: Artificial Sequence
<220> FEATURE:
<223> OTHER INFORMATION: Description of Artificial Sequence: oligo
      primer

<400> SEQUENCE: 8
gcacagaatt catcagtgca caggaggaa gcgctcacgg acg                        43

<210> SEQ ID NO 9
<211> LENGTH: 936
<212> TYPE: DNA
<213> ORGANISM: Homo sapiens
<220> FEATURE:
<221> NAME/KEY: CDS
<222> LOCATION: (25)..(924)

<400> SEQUENCE: 9
```

| gctctccctg ctccagcaag gacc atg agg gcg ctg gag ggg cca ggc atg | 53 |
|---|---|
| Met Arg Ala Leu Glu Gly Pro Gly Leu | |
| 1           5 | |

| tcg ctg ctg tgc ctg gtg ttg gcg ctg cct gcc ctg ctg ccg gtg ccg | 99 |
|---|---|
| Ser Leu Leu Cys Leu Val Leu Ala Leu Pro Ala Leu Leu Pro Val Pro | |
| 10              15              20              25 | |

| gct gta cgc gga gtg gca gaa aca ccc acc tac ccc tgg cgg gac gca | 147 |
|---|---|
| Ala Val Arg Gly Val Ala Glu Thr Pro Thr Tyr Pro Trp Arg Asp Ala | |
|         30              35              40 | |

| gag aca ggg gag cgg ctg gtg tgc gcc cag tgc ccc cca ggc acc ttt | 195 |
|---|---|
| Glu Thr Gly Glu Arg Leu Val Cys Ala Gln Cys Pro Pro Gly Thr Phe | |
| 45              50              55 | |

| gtg cag cgg ccg tgc cgc cga gac agc ccc acg acg tgt ggc ccg tgt | 243 |
|---|---|
| Val Gln Arg Pro Cys Arg Arg Asp Ser Pro Thr Thr Cys Gly Pro Cys | |
|     60              65              70 | |

| cca ccg cgc cac tac acg cag ttc tgg aac tac ctg gag cgc tgc cgc | 291 |
|---|---|
| Pro Pro Arg His Tyr Thr Gln Phe Trp Asn Tyr Leu Glu Arg Cys Arg | |
| 75              80              85 | |

| tac tgc aac gtc ctc tgc ggg gag cgt gag gag gag gca cgg gct tgc | 339 |
|---|---|
| Tyr Cys Asn Val Leu Cys Gly Glu Arg Glu Glu Glu Ala Arg Ala Cys | |
| 90              95              100             105 | |

| cac gcc acc cac aac cgt gcc tgc cgc tgc cgc acc ggc ttc ttc gcg | 387 |
|---|---|
| His Ala Thr His Asn Arg Ala Cys Arg Cys Arg Thr Gly Phe Phe Ala | |
|         110             115             120 | |

-continued

```
cac gct ggt ttc tgc ttg gag cac gca tcg tgt cca cct ggt gcc ggc       435
His Ala Gly Phe Cys Leu Glu His Ala Ser Cys Pro Pro Gly Ala Gly
            125                 130                 135 gtg att gcc ccg ggc acc ccc agc cag aac acg cag tgc cag ccg tgc       483
Val Ile Ala Pro Gly Thr Pro Ser Gln Asn Thr Gln Cys Gln Pro Cys
            140                 145                 150 ccc cca ggc acc ttc tca gcc agc agc tcc agc tca gag cag tgc cag       531
Pro Pro Gly Thr Phe Ser Ala Ser Ser Ser Ser Ser Glu Gln Cys Gln
            155                 160                 165 ccc cac cgc aac tgc acg gcc ctg ggc ctg gcc ctc att gtg cca ggc       579
Pro His Arg Asn Cys Thr Ala Leu Gly Leu Ala Leu Ile Val Pro Gly
170             175                 180                 185 tct tcc tcc cat gac acc ctg tgc acc agc tgc act ggc ttc ccc ctc       627
Ser Ser Ser His Asp Thr Leu Cys Thr Ser Cys Thr Gly Phe Pro Leu
                190                 195                 200 agc acc agg gta cca gga gct gag gag tgt gag cgt gcc gtc atc gac       675
Ser Thr Arg Val Pro Gly Ala Glu Glu Cys Glu Arg Ala Val Ile Asp
            205                 210                 215 ttt gtg gct ttc cag gac atc tcc atc aag agg ctg cag cgg ctg ctg       723
Phe Val Ala Phe Gln Asp Ile Ser Ile Lys Arg Leu Gln Arg Leu Leu
            220                 225                 230 cag gcc ctc gag gcc ccg gag ggc tgg gct ccg aca cca agg gcg ggc       771
Gln Ala Leu Glu Ala Pro Glu Gly Trp Ala Pro Thr Pro Arg Ala Gly
235                 240                 245 cgc gcg gcc ttg cag ctg aag ctg cgt cgg cgg ctc acg gag ctc ctg       819
Arg Ala Ala Leu Gln Leu Lys Leu Arg Arg Arg Leu Thr Glu Leu Leu
250                 255                 260                 265 ggg gcg cag gac ggg gcg ctg ctg gtg cgg ctg ctg cag gcg ctg cgc       867
Gly Ala Gln Asp Gly Ala Leu Leu Val Arg Leu Leu Gln Ala Leu Arg
                270                 275                 280 gtg gcc agg atg ccc ggg ctg gag cgg agc gtc cgt gag cgc ttc ctc       915
Val Ala Arg Met Pro Gly Leu Glu Arg Ser Val Arg Glu Arg Phe Leu
                285                 290                 295 cct gtg cac tgatcctggc cc                                             936
Pro Val His
        300
```